(12) United States Patent
Hageman et al.

(10) Patent No.: US 12,722,012 B2
(45) Date of Patent: Sep. 1, 2026

(54) CLOSED-LOOP DEEP BRAIN STIMULATION (DBS) PROGRAMMING BASED ON EVOKED SIGNALS AND LOCAL FIELD POTENTIAL (LFP) SIGNALS

(71) Applicant: Medtronic, Inc., Minneapolis, MN (US)

(72) Inventors: Kristin N. Hageman, Dayton, MN (US); Scott R. Stanslaski, Shoreview, MN (US); Erik J. Peterson, Fridley, MN (US); Rene A. Molina, Maple Grove, MN (US); Paul H. Stypulkowski, North Oaks, MN (US); David A. Dinsmoor, North Oaks, MN (US); Leonid M. Litvak, Beit Shemesh (IL)

(73) Assignee: Medtronic, Inc., Minneapolis, MN (US)

( * ) Notice: Subject to any disclaimer, the term of this patent is extended or adjusted under 35 U.S.C. 154(b) by 463 days.

(21) Appl. No.: 18/307,585

(22) Filed: Apr. 26, 2023

(65) Prior Publication Data

US 2023/0347152 A1 Nov. 2, 2023

Related U.S. Application Data

(60) Provisional application No. 63/363,984, filed on May 2, 2022.

(51) Int. Cl.
*A61N 1/36* (2006.01)
*A61N 1/02* (2006.01)

(52) U.S. Cl.
CPC ......... *A61N 1/36139* (2013.01); *A61N 1/025* (2013.01)

(58) Field of Classification Search
None
See application file for complete search history.

(56) References Cited

U.S. PATENT DOCUMENTS 8,914,119 B2 12/2014 Wu et al.
9,364,672 B2 6/2016 Marnfeldt
(Continued)

FOREIGN PATENT DOCUMENTS

WO 2019204884 A1 10/2019
WO 2019210371 A1 11/2019
(Continued)

OTHER PUBLICATIONS

International Search Report and Written Opinion of International Application No. PCT/US2023/020244 dated Aug. 11, 2023, 12 pp.
(Continued)

*Primary Examiner* — Benjamin J Klein
*Assistant Examiner* — Willow Grace Welch
(74) *Attorney, Agent, or Firm* — Shumaker & Sieffert, P.A.

(57) ABSTRACT

A system for closed-loop therapy includes memory configured to store a first set of one or more parameters for a first set of therapeutic electrical stimulation signals. The system includes processing circuitry configured to determine one or more local field potential (LFP) measurements of an LFP that is intrinsically generated, cause stimulation generation circuitry to deliver one or more electrical stimulation signals, determine one or more evoked resonant neural activity (ERNA) signals that are evoked by delivery of respective ones of the electrical stimulation signals, determine a second set of one or more parameters for a second set of therapeutic electrical stimulation signals based on the one or more evoked signals and the one or more LFP measurements, and cause the stimulation generation circuitry to deliver the
(Continued)

second set of the one or more therapeutic electrical stimulation signals.

26 Claims, 6 Drawing Sheets

(56) References Cited

U.S. PATENT DOCUMENTS 9,381,356 B2 7/2016 Parker et al.
10,016,370 B2 7/2018 Xia
10,463,860 B2 11/2019 Sinclair et al.
10,688,306 B2 6/2020 Strother et al.
10,849,525 B2 12/2020 Parker et al.
10,953,025 B2 3/2021 Xia
2002/0188330 A1* 12/2002 Gielen ................. A61B 5/4094 607/45
2013/0218232 A1* 8/2013 Giftakis ............... A61N 1/3615 607/45
2016/0287126 A1 10/2016 Parker et al.
2018/0133459 A1 5/2018 Parker et al.
2018/0333582 A1 11/2018 Grill et al.
2019/0381317 A1 12/2019 Sinclair et al.
2020/0138324 A1* 5/2020 Sinclair ................ A61B 5/4836
2020/0215331 A1 7/2020 Single
2020/0269054 A1 8/2020 Dearden et al.
2020/0337645 A1 10/2020 Kremen et al.
2021/0121697 A1 4/2021 Linde et al.
2021/0154476 A1 5/2021 Senderowicz et al.
2022/0047873 A1 2/2022 Ince et al.
2022/0192579 A1* 6/2022 Sinclair ................ A61B 5/4836
2023/0166111 A1* 6/2023 Hageman ............... A61B 5/383 607/59

FOREIGN PATENT DOCUMENTS

WO 2021022332 A1 2/2021
WO 2023100007 A1 6/2023

OTHER PUBLICATIONS

McDermott, Hugh et al., “Feedback control for deep brain stimulation for motor disorders”, Healthcare Technology Letters, vol. 7, No. 3, Jun. 23, 2020, pp. 72-75.
Communication pursuant to Article 94(3) EPC from counterpart European Application No. 23726719.0 dated Apr. 14, 2026, 6 pp.

* cited by examiner

CLOSED-LOOP DEEP BRAIN STIMULATION (DBS) PROGRAMMING BASED ON EVOKED SIGNALS AND LOCAL FIELD POTENTIAL (LFP) SIGNALS

This application claims the benefit of U.S. Provisional Patent Application No. 63/363,984, filed May 2, 2022, the entire contents of which are incorporated herein by reference.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads, and an electrode on a stimulator housing located remotely from the target site (e.g., near clavicle). It may be possible to use leadless stimulation using electrodes mounted on the stimulation housing. Hence, electrical stimulation is used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

This disclosure describes example techniques for processing circuitry to perform closed-loop deep brain stimulation (DBS) programming based on evoked signals and local field potential (LFP). One example of the evoked signal is a evoked resonant neural activity (ERNA) signal. For instance, the processing circuitry may utilize a combination of LFP measurements and evoked signals to determine updates to one or more parameters of a therapeutic electrical stimulation signal. An LFP may be from an intrinsic signal generated within a brain of a patient. That is, the LFP is present without being evoked by delivery of an electrical stimulation; however, characteristics of the LFP may be influenced by delivered stimulation. In some examples, the LFP is generated due to a signal source (e.g., oscillatory signal source) within the brain of the patient. An evoked signal, on the other hand, is an signal that the brain generates (e.g., evokes) in response to an electrical stimulation signal. That is, the evoked signal is not present until after electrical stimulation has been delivered.

In a closed-loop DBS programming system, the processing circuitry may utilize sensed signals to determine whether a change in parameters for a therapeutic electrical stimulation signal is appropriate, and if so, how to change the parameters. However, in some examples, utilizing only one form of sensed signal may be insufficient to determine whether to change parameters, or by how much to change parameters for the therapeutic electrical stimulation signal (e.g., due to lack of quality of signal, insufficient confidence in the signal, or ambiguity as to whether the signal indicates a patient condition). This disclosure describes example ways in which the processing circuitry may utilize multiple sensed signals to determine whether a change in parameters for a therapeutic electrical stimulation signal is appropriate, and if so, how to change the parameters. For instance, the processing circuitry may utilize both LFP measurements and evoked signals to determine whether to change the parameters, and by how much.

In one example, the disclosure describes a system for closed-loop therapy, the system comprising: memory configured to store a first set of one or more parameters for a first set of one or more therapeutic electrical stimulation signals; and processing circuitry coupled to the memory and configured to: determine one or more local field potential (LFP) measurements of an LFP, wherein the LFP is intrinsically generated by a signal source within a brain of the patient; cause stimulation generation circuitry to deliver one or more electrical stimulation signals; determine one or more evoked resonant neural activity (ERNA) signals that are evoked by delivery of respective ones of the one or more electrical stimulation signals; determine a second set of one or more parameters for a second set of one or more therapeutic electrical stimulation signals based on the one or more evoked signals and the one or more LFP measurements, wherein the second set of one or more parameters are updates to the first set of one or more parameters; and cause the stimulation generation circuitry to deliver the second set of the one or more therapeutic electrical stimulation signals.

In one example, the disclosure describes a method for closed-loop therapy, the method comprising: storing a first set of one or more parameters for a first set of one or more therapeutic electrical stimulation signals; determining one or more local field potential (LFP) measurements of an LFP, wherein the LFP is intrinsically generated by a signal source within a brain of the patient; causing stimulation generation circuitry to deliver one or more electrical stimulation signals; determining one or more evoked resonant neural activity (ERNA) signals that are evoked by delivery of respective ones of the one or more electrical stimulation signals; determining a second set of one or more parameters for a second set of one or more therapeutic electrical stimulation signals based on the one or more evoked signals and the one or more LFP measurements, wherein the second set of one or more parameters are updates to the first set of one or more parameters; and causing the stimulation generation circuitry to deliver the second set of the one or more therapeutic electrical stimulation signals.

In one example, the disclosure describes a computer-readable storage medium storing instructions thereon that when executed cause one or more processors to: store a first set of one or more parameters for a first set of one or more therapeutic electrical stimulation signals; determine one or more local field potential (LFP) measurements of an LFP, wherein the LFP is intrinsically generated by a signal source within a brain of the patient; cause stimulation generation circuitry to deliver one or more electrical stimulation signals; determine one or more evoked resonant neural activity (ERNA) signals that are evoked by delivery of respective ones of the one or more electrical stimulation signals; determine a second set of one or more parameters for a second set of one or more therapeutic electrical stimulation signals based on the one or more evoked signals and the one or more LFP measurements, wherein the second set of one or more parameters are updates to the first set of one or more parameters; and cause the stimulation generation circuitry to deliver the second set of the one or more therapeutic electrical stimulation signals.

In one example, the disclosure describes a system for closed-loop therapy, the system comprising: means for storing a first set of one or more parameters for a first set of one or more therapeutic electrical stimulation signals; means for determining one or more local field potential (LFP) measurements of an LFP, wherein the LFP is intrinsically generated by a signal source within a brain of the patient; means for causing stimulation generation circuitry to deliver one or more electrical stimulation signals; means for determining one or more evoked resonant neural activity (ERNA) signals that are evoked by delivery of respective ones of the one or more electrical stimulation signals; means for determining a second set of one or more parameters for a second set of one or more therapeutic electrical stimulation signals based on the one or more evoked signals and the one or more LFP measurements, wherein the second set of one or more parameters are updates to the first set of one or more parameters; and means for causing the stimulation generation circuitry to deliver the second set of the one or more therapeutic electrical stimulation signals.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
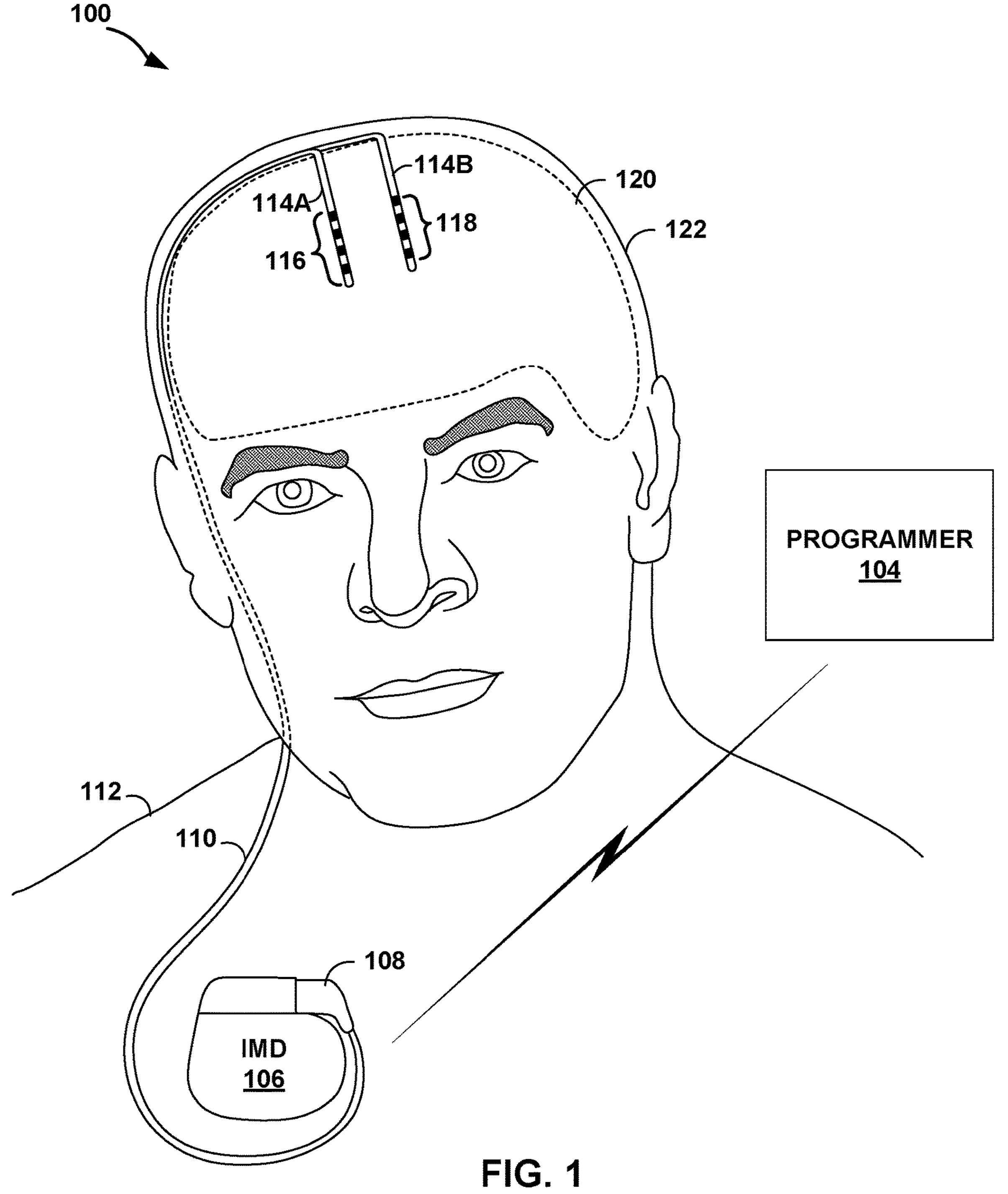
FIG. 1 is a conceptual diagram illustrating an example system that includes an implantable medical device (IMD) configured to deliver deep brain stimulation (DBS) to a patient according to an example of the techniques of the disclosure.

This disclosure describes example techniques to automatically determine parameters for a therapeutic electrical stimulation signal. The example techniques are described with respect to deep brain stimulation (DBS), but the example techniques are not so limited and may be applied to other types of therapies and/or other anatomical locations. DBS may provide relief for many different patient conditions such as essential tremors (ETs), Parkinson's, obsessive compulsive disorder (OCD), depression, and others. For DBS, a surgeon implants one or more leads within the brain of the patient for outputting therapeutic electrical stimulation signals at depth within the brain. The one or more leads are coupled to an implantable medical device (IMD) that generates the therapeutic electrical stimulation signals for delivery through the one or more leads.

After implantation, the surgeon/clinician may be tasked with determining what the parameters should be for the therapeutic electrical stimulation signals. The IMD may then generate the therapeutic electrical stimulation signals in accordance with the determined parameters. However, over time the efficacy of the therapeutic electrical stimulation signals may change. For instance, if there is lead migration, the therapeutic electrical stimulation signals may be insufficient to provide adequate therapeutic relief. If the patient condition worsens, such as due to disease progression or therapy accommodation, the therapeutic electrical stimulation signals may become insufficient to provide adequate therapeutic relief.

There may be other examples for why the therapeutic electrical stimulation signals may be insufficient to provide adequate therapeutic relief. Also, there may be instances where a patient condition may improve (e.g., due to medication supplementing the stimulation therapy). In such cases, the intensity of the therapeutic electrical stimulation signals may be greater than needed to provide effective therapy.

This disclosure describes example closed-loop techniques in which processing circuitry may utilize sensed signals as feedback to determine whether to change one or more parameters of the therapeutic electrical stimulation signals. The processing circuitry may be part of the IMD, an external programmer, a cloud computing environment, or any combination thereof. For instance, the processing circuitry configured to perform one or more example techniques described in this disclosure may include the processing circuitry of just the IMD, the programmer, or the cloud computing environment, or any combination of the processing circuitry of the IMD, the programmer, and the cloud computing environment.

In one or more examples described in this disclosure, if there is a reduction in the efficacy of the therapeutic electrical stimulation signals, processing circuitry may be configured to update one or more parameters of the therapeutic electrical stimulation signals to increase the efficacy. Alternatively or additionally, the processing circuitry may be configured to update one or more parameters of the therapeutic electrical stimulation signals to limit undesirable side effects. Because the processing circuitry may determine updates to the one or more parameters in a closed-loop manner, the processing circuitry may determine updated parameters relatively quickly, and with minimal patient or clinician intervention, which may minimize the amount of time the patient experiences a reduction in therapeutic efficacy.

The examples of the sensed signals that the processing circuitry may utilize for the closed-loop techniques include local field potential (LFP) measurements and evoked signals, such as evoked resonant neural activity (ERNA) signals, to determine whether parameters for the therapeutic electrical stimulation signal are to be changed, and if so, by how much. As described above, an LFP may be an intrinsic signal within the brain of the patient. In some cases, the LFP is intrinsically generated by a signal source within the brain of the patient. The signal characteristics of the LFP may be indicative of a patient condition (e.g., brain state). An evoked signal is not an intrinsic signal within the brain of the patient, but is evoked due to a stimulation signal being delivered to the brain. The evoked signal and the LFP may be different in frequency component and amplitude as well. The stimulation signal delivered to the brain that evokes the evoked signal need not necessarily provide any therapeutic benefit, although it is possible for the stimulation signal that evokes the evoked signal to provide therapeutic benefit.

In some examples, the processing circuitry may store a first set of one or more parameters for a first set of therapeutic electrical stimulation signals. As one example, the first set of one or more parameters may be initial parameters determined shortly after implantation in a clinician setting. The processing circuitry may receive the first set of one or more parameters for storage in memory. As another example, the first set of one or more parameters may be parameters that were updated from the initial parameters, but are due for further updating. For instance, the processing circuitry may have determined updates to the initial parameters, and stored the updated initial parameters in memory.

The processing circuitry may determine one or more LFP measurements of an LFP. In some examples, the processing circuitry may also determine one or more evoked signals. Because the evoked signals are evoked, the processing circuitry may cause the stimulation generation circuitry to deliver one or more electrical stimulation signals, and determine one or more evoked signals that are evoked by delivery of respective ones of the one or more electrical stimulation signals. The processing circuitry may determine a second set of one or more parameters for a second set of one or more therapeutic electrical stimulation signals based on the one or more evoked signals and the one or more LFP measurements. The second set of one or more parameters may be updates to the first set of one or more parameters.

There may be various ways in which the processing circuitry may determine the second set of one or more parameters for the second set of one or more therapeutic electrical stimulation signals based on the one or more evoked signals and the one or more LFP measurements. As one example, the processing circuitry may utilize a first sensed signal to determine whether to determine a second sensed signal. For instance, the processing circuitry may determine the one or more LFP measurements (e.g., by receiving the one or more LFP measurements from sensing circuitry). The processing circuitry may evaluate the one or more LFP measurements, such as determining whether there is a change in the one or more current LFP measurements relative to one or more previous LFP measurements. If there is a change, the processing circuitry may determine the one or more evoked signals (e.g., by causing the stimulation generation circuitry to deliver one or more electrical stimulation signals).

As another example, the processing circuitry may determine whether there is no change (e.g., any change is less than a threshold signal level) in the LFP measurements for a period of time. If there is no change, the processing circuitry may determine the one or more evoked signals. As another example, the processing circuitry may determine that the one or more LFP measurements are greater than or below a threshold signal level for a period of time, and determine the one or more evoked signals based on the determination that the one or more LFP measurements are greater than or below the threshold signal level for the period of time. As further example, the processing circuitry may determine that the one or more LFP measurements include artifacts, and determine the one or more evoked signals based on the determination that the one or more LFP measurements include artifacts.

The processing circuitry may use the evoked signals or a combination of the LFP measurements and the evoked signals to determine whether to update the first set of one or more therapy parameters to the second set of one or more therapy parameters based on the evoked signals or the combination of the LFP measurements and the evoked signals. In the above example, the processing circuitry utilized the LFP measurements to trigger a determination of the one or more evoked signals. However, the example techniques are not so limited, in some examples, the processing circuitry may determine the one or more evoked signals first, and based on the one or more evoked signals trigger determination of the one or more LFP measurements.

The sensing circuitry may be able to sense the LFP measurements even during delivery of therapeutic electrical stimulation signals. However, in some cases, the processing circuitry may cease delivery of therapeutic electrical stimulation signals so that there is a time window within which the processing circuitry can determine the one or more evoked signals. Accordingly, in some examples, the processing circuitry may determine one or more LFP measurements during the delivery of the first set of the one or more therapeutic electrical stimulation signals according to the first set of one or more parameters. Then, based on the LFP measurements, selectively determine the one or more evoked signals. In this way, power consumption may be reduced by selectively determining the one or more evoked signals based on the LFP measurements because the power that is consumed delivering the electrical stimulation signals that evoke the evoked signals may not be consumed. In some examples, the processing circuitry may determine the LFP measurements, including whether there is a change in the LFP measurements, during an instance where there is no delivery of therapeutic electrical stimulation signals.

In the above examples, one of the sensed signals (e.g., LFP measurements or evoked signals) triggers the determination of the other signal (e.g., LFP measurement trigger determination of evoked signals, or vice-versa). However, the example techniques are not so limited. In some examples, the processing circuitry may be configured to determine both LFP measurements and evoked signals, without necessarily one signal triggering the determination of another. For instance, in some examples, there may be an increase in confidence that parameters should be updated by evaluating changes in both the LFP measurements and the evoked signals.

After the processing circuitry determines a second set of one or more parameters for a second set of one or more therapeutic electrical stimulation signals based on the one or more evoked signals and the one or more LFP measurements, the processing circuitry may cause the stimulation generation circuitry to deliver the second set of one or more therapeutic electrical stimulation signals. The stimulation generation circuitry may generate the second set of one or more therapeutic electrical stimulation signal according to the second set of one or more parameters that the processing circuitry determined based on the one or more evoked signals and the one or more LFP measurements.

FIG. 1 is a conceptual diagram illustrating an example system 100 that includes an implantable medical device (IMD) 106 configured to deliver deep brain stimulation to a patient 112. In some examples, the DBS may be closed-loop in the sense that IMD 106, as one example, may adjust, increase, or decrease the magnitude of one or more parameters of the DBS in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation, sense intrinsic neuronal signals, and sense neural signals that are evoked in response to delivery of stimulation. System 100 may be configured to treat a patient condition, such as a movement disorder (e.g., essential tremor (ET) or Parkinson's), neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease or essential tremor (ET). However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus (STN), globus pallidus or thalamus, ventralus intermediate (VIM), anterior nucleus (ANT), ventral internal capsule/ventral striatum (VCVS), cortico-basal ganglia-thalamocortical circuit, or anterior insular cortex (AIC), may be an effective treatment to manage disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver electrical stimulation to brain 120. In other examples, all of electrodes 116, 118 are configured to both sense neurological brain signals and deliver electrical stimulation to brain 120. In some examples, unipolar stimulation may be possible where one electrode is on the housing of IMD 106.

IMD 106 includes a therapy module (e.g., which may include processing circuitry or other electrical circuitry configured to perform the functions attributed to IMD 106) that includes stimulation generation circuitry configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. There may be various examples of neurological brain signals that electrodes 116, 118 may be configured to sense. One example of a neurological brain signal is a local field potential (LFP). An LFP may be an intrinsic signal within brain 120 of patient 112 that is generated by a signal source within brain 120 of patient 112. Another example of a neurological brain signal is an evoked signal, such as an evoked resonant neural activity (ERNA) signal. For ease of illustration, the example techniques are described with respect to an ERNA signal as an evoked signal, but the example techniques should not be considered limited to an ERNA signal. Delivery of electrical stimulation within brain 120 may evoke an ERNA signal, and the ERNA signal may not be an intrinsic signal. The electrical stimulation delivered within brain 120 to evoke the ERNA signal need not necessarily provide therapeutic benefit, but therapeutic benefit from the electrical stimulation used to evoke the ERNA signal is possible. Electroencephalogram (EEG) signal or an electrocorticogram (ECoG) signal are also examples of neurological signals. For example, neurons generate the neurological signals, and if measured at depth, it is LFP or ERNA (if evoked), if measured on the dura, it is ECoG, and if on scalp, it is EEG.

In some examples, the delivery of therapeutic electrical stimulation signals may be based on a feature of interest (e.g., biomarker). One example of the feature of interest (e.g., biomarker) within the LFPs is synchronized beta frequency band (8-33 Hz) LFP activity recorded within the sensorimotor region of the subthalamic nucleus (STN) in Parkinson's disease or essential tremor patients. The source of the LFP activity can be considered as a signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the LFP source that is within the beta frequency band) by both medication and DBS may correlate with improvements in the motor symptoms of patients who have Parkinson's disease or essential tremor.

For example, one or more of electrodes 116 and/or 118 may sense the LFP activity. Accordingly, there may be a plurality of LFP measurements of an LFP, where each of the LFP measurements may be measured with different electrodes 116 and/or 118 on leads 114A, 114B or by the same electrodes 116 and/or 118 on leads 114A, 114B. As described, the LFP is intrinsically generated by a signal source (e.g., oscillatory electrical voltage source) within brain 120 of patient 122.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing neurological brain signals.

Therapeutic electrical stimulation generated by IMD 106 may be configured to manage a variety of disorders and conditions. In some examples, the stimulation generation circuitry of IMD 106 is configured to generate and deliver therapeutic electrical stimulation pulses to patient 112 via electrodes of a selected stimulation electrode combination. However, in other examples, the stimulation generation circuitry of IMD 106 may be configured to generate and deliver a continuous wave signal, e.g., a sine wave or triangle wave. In either case, stimulation generation circuitry within IMD 106 may generate the electrical stimulation therapy for DBS according to a selected therapy program. In examples in which IMD 106 delivers therapeutic electrical stimulation in the form of stimulation pulses, a therapy program may include a set of therapy parameter values (e.g., parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver therapeutic stimulation signals to tissue of patient 112 and the respective polarities of the selected electrodes.

In some examples, electrodes 116, 118 may be circumferentially-segmented DBS arrays of electrodes, and include some non-segmented electrodes as well, such as ring electrodes. Circumferentially-segmented DBS arrays refer to electrodes that are segmented circumferentially along the lead. As one example, leads 114A and 114B may include a first set of electrodes arranged circumferentially around leads 114A and 114B that are all at the same height level on leads 114A and 114B. Each of the electrodes in the first set of electrodes is a separate segmented electrode and form a level of circumferentially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of circumferentially-segmented array of electrodes. The electrodes may be beneficial by enabling directional stimulation and sensing.

With the electrodes, IMD 106 may be configured to perform both directional stimulation and sensing, thereby enhancing the ability to target the source of the LFP activities (also referred to as pathological neuronal activities). For example, IMD 106 may be configured to perform directional sensing to determine a direction and/or orientation of the LFP source (e.g., signal source that generates the LFP) having the signal component in the beta frequency band. IMD 106 may direct the electrical stimulation toward the signal source to suppress (e.g., squelch) the signal component produced by the signal source in the beta frequency band, as one example. This disclosure describes example techniques to utilize ERNA signals to determine the parameters of the therapeutic electrical stimulation signals used to suppress the signal component produced by the signal source in the beta frequency band.

The signal component in the beta frequency band is described as one example, and the techniques are applicable to other types of LFP activity. Also, the example techniques should not be considered as being limited to suppressing signal components produced by the signal source. The example techniques may be used generally for DBS, or other types of therapy where a combination of LFP measurements and ERNA signals are used as part of closed-loop therapy.

Furthermore, the example techniques are not limited to examples where one or more of electrodes 116, 118 are circumferentially-segmented electrodes. The example of using circumferentially-segmented electrodes is described as a way of directional stimulation and sensing. However, the example techniques are also useable in examples where directional stimulation and sensing are not available or are not used. Moreover, there may be other ways of performing directional stimulation and sensing that do not require the use of circumferentially-segmented electrodes.

As an example, to suppress the signal component having the beta frequency band from the LFP source (e.g., the signal source of the LFP), IMD 106 may output an electrical stimulation signal that alters the way in which neurons of the LFP source produce signals. For example, the electrical stimulation either directly inhibits a certain neuronal population that includes the LFP source or excites one group of neurons which in turn suppresses another group of neurons (e.g., network effect). The stimulation may act on the neurons directly, and not necessarily on the signals the neurons (e.g., LFP source) produces.

In an example, for DBS, IMD 106 may be configured to deliver therapeutic electrical stimulation signals based on one or more parameters such as amplitude, pulse width, and frequency. In some examples, shortly after implantation or during the implantation surgery for IMD 106 and/or leads 114A, 114B, a clinician/surgeon may determine initial parameters (e.g., a first set of one or more parameters for a first set of one or more therapeutic electrical stimulation signals). However, the effectiveness of the first set of one or more therapeutic electrical stimulation signals may change overtime. For instance, due to lead migration, accommodation of the neural substrate to stimulation, or worsening of patient condition, the first set of one or more therapeutic electrical stimulation signals may be insufficient to provide effective therapy. Conversely, if patient condition improves, the intensity of the first set of one or more therapeutic electrical stimulation signals may be greater than needed to provide effective therapy.

Accordingly, there may be benefit in periodically, or possibly continuously, updating the first set of one or more parameters to a second set of one or more parameters for a second set of one or more therapeutic electrical stimulation signals. In the above examples, there may be benefit in updating the initial parameters. However, in some cases, after the initial parameters are updated, there may be benefit in periodically, or possibly continuously, determining whether to update the parameters for therapeutic electrical stimulation signals.

One way to update the parameters for therapeutic electrical stimulation signals may be for patient 112 to periodically schedule an appointment with a clinician to update the parameters. Another way to update the parameters for therapeutic electrical stimulation signals may be for patient 112 to manually adjust the parameters himself/herself. In both such examples, there may be burden on patient 112 to have to schedule appointments for parameter adjustment or self-titrate the parameters. This may also lead to delay in updates to parameters.

This disclosure describes example techniques for closed-loop parameter adjustment. For example, the processing circuitry of IMD 106 may be configured to determine one or more LFP measurements of an LFP. In addition, the processing circuitry of IMD 106 may be configured to determine one or more evoked (e.g., ERNA) signals. To determine the one or more evoked signals, the processing circuitry of IMD 106 may cause the stimulation generation circuitry of IMD 106 to deliver one or more electrical stimulation signals, and determine one or more evoked signals (e.g., ERNA signals) that are evoked by delivery of respective ones of the one or more electrical stimulation signals.

The processing circuitry of IMD 106 may utilize both LFP measurements and the evoked (e.g., ERNA) signals to determine whether to update, and by how much to update, the parameters for therapeutic electrical stimulation signals. For example, the processing circuitry of IMD 106 may be configured to determine one or more LFP measurements of an LFP, with each of the LFP measurements being measured with different electrodes 116, 118 on leads 114A, 114B or same electrodes 116, 118 on leads 114A, 114B. As one example, one of electrodes 118 may be a reference electrode (e.g., ground), and the processing circuitry may receive a first LFP measurement that is sensed by a first one of electrodes 116 relative to the reference electrode of electrodes 118. The processing circuitry may receive a second LFP measurement that is sensed by a second one of electrodes 116 relative to the reference electrode of electrodes 118, and so forth.

Although the above examples describe the reference electrode being one of electrodes 118, and receiving the LFP measurements through electrodes 116, the techniques are not so limited. In some examples, the reference electrode may be one of electrodes 116, and the processing circuitry may receive the LFP measurements through electrodes 118. In some examples, the reference electrode need not be one of electrodes 116 or 118, and may be another electrode, such as an electrode on the housing of IMD 106.

Examples where the reference electrode is on one of leads 114A or 114B, and the other electrode used for sensing the LFP (e.g., determining the LFP measurement) is on the other of leads 114A or 114B or on the housing of IMD 106 is referred to as a monopolar sensing. In some examples, to determine the LFP measurements, the processing circuitry may receive bipolar sensing measurements. In bipolar sensing measurements, electrodes 116, 118 for sensing are on the same one of leads 114A, 114B.

For ease of description, this disclosure describes monopolar sensing, but the example techniques are applicable to bipolar sensing as well. Also, for ease of description, for monopolar sensing, the example techniques are described with respect to the reference electrode being one of electrodes 118, and other electrode used for sensing being one of electrodes 116.

Although not required, in some examples, the processing circuitry of IMD 106 may be configured to determine one or more electrodes 116 on lead 114A for delivering therapeutic electrical stimulation signal based on the LFP measurements. However, the example techniques are not so limited. In some examples, a clinician may manually select which electrodes 116 on lead 114A are configured to deliver therapeutic electrical stimulation signals.

As one example, processing circuitry of IMD 106 may determine which LFP measurement had the highest powered beta band signal (e.g., signal in 8-33 Hz of the LFP measurement) of electrodes 116, and may determine that the one of electrodes 116 having the LFP measurement with highest powered beta band signal is the electrode of electrodes 116 to use for delivery of therapeutic electrical stimulation signal. The return electrode for the therapeutic stimulation signal may be an electrode on the housing of IMD 106 or may be one of electrodes 116, 118.

There may be various ways in which to determine the LFP measurement having the highest powered beta band signal. In some examples, the LFP measurements are time-varying, and can possibly be sinusoidal.

This disclosure describes using current source density (CSD) as a way in which to determine the highest powered beta band signal, but the example techniques should not be considered limited to using CSD for determining the highest powered beta band signal. For example, the processing circuitry may bandpass filter the LFP measurement so that the frequency components in the beta band remain (e.g., filter out frequency components that are not in beta band). Instead of or in addition to CSD, the processing circuitry of IMD 106 may determine root-mean-square (RMS) value of the LFP measurements, and determine the LFP measurement having the largest RMS value. As another example, electrodes 116 may be coupled to a full-bridge or half-bridge rectifier. The processing circuitry may receive rectified LFP measurements, and determine an average of the rectified LFP measurements. The processing circuitry may determine the rectified LFP measurement having the highest average value. As another example, the processing circuitry may determine the maximum amplitude of the LFP measurements.

As another example, in addition to or instead of CSD, the processing circuitry may utilize power spectral density (PSD). In PSD, the processing circuitry may determine a transform (e.g., Fourier transform, such as a fast Fourier transform (FFT)) to convert the LFP measurements into a frequency domain, and determine the power spectral density. The processing circuitry may remove the lowest power spectral density for normalization. The processing circuitry may determine the power spectral density in the beta band as one example way to determine the LFP measurements.

Also, the use of beta band is described as an example, and should not be considered limiting. In some examples, the processing circuitry may determine the LFP measurement having the highest power overall, and not just at the beta band. In some examples, the processing circuitry may determine the LFP measurement having the highest power at a frequency band other than the beta band. For example, the processing circuitry may determine the LFP measurement having the highest power in the 4-8 Hz band (e.g., theta band) or the 35-100 Hz band (e.g., gamma band).

Determining the LFP measurement with the highest CSD or any of the other example values described above may correlate with one or more electrodes 116 that are most proximal to the signal source that generates the LFP. That is, the electrode of electrodes 116 that is most proximal to the signal source that generates the LFP may also be the electrode of electrodes 116 having the highest CSD for the LFP measurement. In general, the electrodes of electrodes 116 and 118 that are most proximal to the LFP source tend to be the electrodes with which electrical stimulation should be delivered. Electrodes of electrodes 116 and 118 that are most proximal to the LFP source may be the electrodes having the highest current source density (CSD). For instance, electrodes of electrodes 116 and 118 that have the highest CSD are also the closest to the LFP source. However, the example techniques do not require selecting electrodes 116 or 118 that are most proximal to the signal source.

In this way, the processing circuitry of IMD 106 may determine one or more electrodes 116 on lead 104A for delivering therapeutic electrical stimulation signal based on the LFP measurements. The processing circuitry of IMD 106 may also determine the parameters for the therapeutic electrical stimulation signal. One example way to determine the parameters for the therapeutic electrical stimulation signal is based on ERNA signals.

The following describes one example way in which to determine parameters for the therapeutic electrical stimulation signal based on ERNA signals. However, the example techniques are not so limited. For instance, for initial parameters, a clinician may manually titrate parameters until the right parameters are identified for the initial therapeutic electrical stimulation signal.

For determining parameters based on ERNA signals, the processing circuitry of IMD 106 may cause the stimulation generation circuitry of IMD 106 to deliver a plurality of electrical stimulation signals via the determined one or more electrodes 116. In one or more examples, the plurality of electrical stimulation signals each include at least one different therapy parameter. For each of the plurality of electrical stimulation signals, the processing circuitry of IMD 106 may determine respective ERNA signals, where the respective ERNA signals are evoked by delivery of the respective plurality of electrical stimulation signals. The processing circuitry may determine parameters for the therapeutic electrical stimulation signal based on the respective ERNA signals.

In this disclosure, the phrase "therapeutic electrical stimulation signal" is used to refer to electrical stimulation signal that is delivered for providing therapy. Delivery of the therapeutic electrical stimulation signal may evoke an ERNA signal, but the techniques do not require the therapeutic electrical stimulation signal to evoke an ERNA signal. The phrase "electrical stimulation signal" is used to refer to electrical stimulation signal that is delivered for evoking an ERNA signal. Delivery of an electrical stimulation signal for evoking an ERNA signal may provide therapeutic effect, but the techniques do not require the electrical stimulation signal used for evoking an ERNA signal to provide therapeutic effect.

As described above, the processing circuitry may cause stimulation generation circuitry to deliver a plurality of electrical stimulation signals via the determined one or more electrodes, where the plurality of electrical stimulation signals each include at least one different therapy parameter. For instance, the processing circuitry may cause the stimulation generation circuitry to sweep across a range of frequencies such that frequency of each of the electrical stimulation signals is different. That is, the processing circuitry may be configured to cause the stimulation generation circuitry to deliver the plurality of electrical stimulation signals via the determined one or more electrodes, where a frequency for each of the plurality of electrical stimulation signals is within a range of frequencies (e.g., 5 Hz to 220 Hz). As another example, the processing circuitry may cause the stimulation generation circuitry to sweep across a range of amplitudes and/or pulse widths such that the amplitude and/or pulse width of each of the electrical stimulation signals is different. That is, the processing circuitry may be configured to cause the stimulation generation circuitry to deliver the plurality of electrical stimulation signals via the determined one or more electrodes, where an amplitude and/or pulse width for each of the plurality of electrical stimulation signals is within a range of amplitudes and/or pulse widths.

The processing circuitry may evaluate the respective ERNA signals for determining the parameters for the therapeutic electrical stimulation signal. For instance, the processing circuitry may determine characteristics of the respective ERNA signals such as resonant activity. Examples of resonant activity include one or more of peak-to-trough amplitude, time between peak-to-peak, decay time constant, change in peak amplitudes (e.g., damping), amount of oscillations (e.g., number of peaks), rise or fall times, and frequency shift from early resonance to late resonance of the respective ERNA signals.

Based on the determined resonant activity, the processing circuitry may select one of the ERNA signals. As an example, the processing circuitry may select the ERNA signal of the respective ERNA signals having the highest peak-to-trough amplitude. As another example, the processing circuitry may select the ERNA signal of the respective ERNA signals having the most of amount of oscillations (e.g., the most number of peaks before the ERNA signals dampens to noise level). As another example, the processing circuitry may select the ERNA signal of the respective ERNA signals having the fastest reduction in peak amplitudes (e.g., fastest damping). The above provide a few non-limiting examples resonant activity that the processing circuitry may evaluate to select an ERNA signal, and other examples of resonant activity are possible. Also, the processing circuitry may select an ERNA signal based on a combination of the resonant activity (e.g., a weighting of two or more examples the resonant activity).

The processing circuitry may determine the respective electrical stimulation signal of the selected ERNA signal, and may determine the parameters of the determined respective electrical stimulation signal. The processing circuitry may determine the parameters for the therapeutic electrical stimulation signal based on the determined parameters. In this way, the processing circuitry may determine parameters for the therapeutic electrical stimulation signal based on the respective ERNA signals.

Regardless of how the parameters of the therapeutic electrical stimulation signals are determined, there may be benefit in periodically determining whether to update the parameters, and if so, by how much. In accordance with one or more examples described in this disclosure, processing circuitry of IMD 106 may be configured to utilize both LFP measurements and ERNA signals to determine to update the parameters, and if so, by how much.

For example, the processing circuitry of IMD 106 may cause the stimulation generation circuitry to deliver a first set of one or more therapeutic electrical stimulation signals according to a first set of one or more parameters. The processing circuitry may determine the first set of one or more parameters using the above example techniques (e.g., by evaluating ERNA signals). As another example, the processing circuitry may determine the first set of one or more parameters based on a clinician programing the first set of one or more parameters. The processing circuitry may store the first set of one or more parameters for a first set of one or more therapeutic electrical stimulation signals in memory.

At some later time, the processing circuitry may determine one or more LFP measurements of an LFP, where the LFP is intrinsically generated by a signal source within brain 120 of patient 112. Also, at this later time, the processing circuitry may determine one or more ERNA signals. To determine the one or more ERNA signals, the processing circuitry may cause the stimulation generation circuitry to deliver one or more electrical stimulation signals, and determine the one or more ERNA signals that are evoked by delivery of respective ones of the one or more electrical stimulation signals. The processing circuitry may determine a second set of one or more parameters for a second set of one or more therapeutic electrical stimulation signals based on the one or more ERNA signals and the one or more LFP measurements, and cause the stimulation generation circuitry to deliver the second set of the one or more therapeutic electrical stimulation signals. The second set of one or more parameters may be updates to the first set of one or more parameters.

For example, to determine the second set of one or more parameters for the second set of one or more therapeutic electrical stimulation signals, the processing circuitry may evaluate the LFP measurements and ERNA signals. In general, different features of the LFP measurements and ERNA signals may be used to determine how to maintain therapy and/or track disease state or medication.

As an example, the processing circuitry may determine peak amplitudes of the LFP measurements and ERNA signals, latency of the LFP measurements and ERNA signals, etc. In some examples, the processing circuitry may determine whether there are changes to the LFP measurements and ERNA signals. For instance, the processing circuitry may compare the characteristics of the current LFP measurements and ERNA signals to characteristics of previous LFP measurements and ERNA signals. Based on the comparison, the processing circuitry may determine whether to change the parameters for the therapeutic electrical stimulation signals, and by how much. Examples of the characteristics of the LFP measurements include amplitude, frequency, etc. Examples of the characteristics of the ERNA signals includes amplitude, latency of peak, timing between peaks, number of peaks, etc.

For example, if the characteristics of current LFP measurements and ERNA signals deviate the characteristics of previous LFP measurements and ERNA signals by a threshold signal level, the processing circuitry may update the parameters, and cause the stimulation generation circuitry to deliver therapeutic electrical stimulation signals having the updated parameters. The processing circuitry may repeat these example operations until the current LFP measurements and ERNA signals are approximately equal to target characteristics of the LFP measurements and ERNA signals.

The previous LFP measurements and/or ERNA signals need not necessarily be the immediately preceding LFP measurements or ERNA signals. In some examples, the processing circuitry may track a history of the LFP measurements and/or ERNA signals across pulses for seconds or minutes. The processing circuitry may utilize the history of LFP measurements and/or ERNA signals as comparison to the current LFP measurements and/or ERNA signals to determine a trend in the LFP measurements and/or ERNA signals, and update the parameters accordingly.

As another example, IMD 106 may store templates of LFP measurements and ERNA signals indicative of a healthy patient. For instance, the templates may be based on LFP measurements and ERNA signals from a population of healthy individuals. In some examples, the templates may be based on LFP measurements and ERNA signals of patient 112 after patient 112 took medication to alleviate symptoms. In some examples, the templates may be based on LFP measurements and ERNA signals of patient 112 in different positions or movements. Another example of a template may be information indicative of a constant amplitude of the ERNA signals, desired amount of latency of peaks, timing between resonant peaks, number of peaks, etc.

The processing circuitry may compare current LFP measurements and ERNA signals to one or more of the example templates, and based on comparison determine whether to update the parameters, and by how much. For example, if one or more characteristics of the current LFP measurements and ERNA signals deviate from one or more characteristics of the template LFP measurements and ERNA signals, the processing circuitry may update the parameters, and cause the stimulation generation circuitry to deliver therapeutic electrical stimulation signals having the updated parameters. The processing circuitry may repeat these example operations until the current LFP measurements and ERNA signals are approximately equal to target characteristics of the LFP measurements and ERNA signals (e.g., characteristics of the template LFP measurements and ERNA signals). In some examples, the template may be periodically updated.

In this way, the processing circuitry may utilize both LFP measurements and ERNA signals in a closed-loop manner to determine parameters for therapeutic electrical stimulation signals. For instance, as some of the examples described above, the characteristics used as feedback for a closed-loop system include peak amplitudes, changes in amplitude correlated with medication, movement, etc., latency, changes in latency of peak, timing between resonant peaks, number of peaks/resonance. Based on these characteristics (e.g., such as comparison to target characteristics such as previous or template characteristics), the processing circuitry may update parameters such as amplitude, frequency, and/or pulse width of the therapeutic electrical stimulations signals.

The above described some example ways in which both LFP measurements and ERNA signals may be used to determine updates to parameters for therapeutic electrical stimulation signals. However, the example techniques are not so limited. In some examples, one of the LFP measurements or ERNA signals may be trigger the determination of the other of the LFP measurements or ERNA signals to determine whether to update the parameters for therapeutic electrical stimulation signals. Since one of LFP measurements or ERNA signals trigger the determination of the other one of LFP measurement or ERNA signals, the example techniques may be considered as determining therapeutic electrical stimulation signals based on the one or more ERNA signal and the one or more LFP measurements.

For example, because determining ERNA signals includes delivery of electrical stimulation signals, there may be additional power consumption for determining ERNA signals. Also, after delivery of an electrical stimulation signal to evoke an ERNA signal, there may be a window during which no stimulation is provided so that there is time to sense the ERNA signal. However, it may be possible to determine the LFP measurements even when IMD 106 is delivering therapeutic electrical stimulation signals.

In one or more examples, the processing circuitry may determine the one or more LFP measurements of an LFP. The processing circuitry may evaluate the one or more LFP measurements, and determine whether or not to determine one or more ERNA signals for purposes of determining updates to the therapeutic electrical stimulation signals.

For instance, similar to above, the processing circuitry may compare one or more current LFP measurements to one or more target LFP measurements. Examples of the target LFP measurements include one or more previous LFP measurements and/or one or more LFP measurements stored in a template. If characteristics of the current LFP measurements deviate from the characteristics of the target LFP measurements by a threshold signal level, the processing circuitry may determine that a determination of one or more ERNA signals should be made. If, however, the characteristics of the current LFP measurements do not deviate from the characteristics of the target LFP measurements by the threshold signal level, the processing circuitry may determine to bypass determination of the ERNA signals.

In response to determining that a determination of one or more ERNA signals should be made, the processing circuitry may cause the stimulation generation circuitry to deliver one or more electrical stimulation signals, and determine the one or more ERNA signals evoked in response to the delivery of the one or more electrical stimulation signals. The processing circuitry may compare the one or more ERNA signals (e.g., current ERNA signals) to one or more target ERNA signals (e.g., previous ERNA signals or template ERNA signals). If the processing circuitry determines that the characteristics of the one or more ERNA signals deviate from the characteristics of the target ERNA signals by a threshold signal level, the processing circuitry may determine updated parameters. If, however, the characteristics of the current ERNA signals do not deviate from the characteristics of the target ERNA signals by the threshold signal level, the processing circuitry may determine to bypass determination of updated parameters.

In some examples, the processing circuitry of IMD 106 may cause IMD 106 deliver therapeutic electrical stimulation signals based on LFP measurements, and without relying on ERNA signals. The processing circuitry may adjust the parameters until the therapeutic electrical stimulation signals cause the LFP to suppress. In such examples, because the LFP is suppressed, the processing circuitry may further update the parameters based on ERNA signals. In this way, the processing circuitry may determine a set of one or more parameters for a set of one or more therapeutic electrical stimulation signals based on the one or more ERNA signals and the one or more LFP measurements. That is, the processing circuitry may use the one or more LFP measurements to determine parameters that cause the LFP to suppress, and then use the ERNA signals for further updating.

As an example, the processing circuitry may be configured to determine that there is a change in the LFP measurements, as described above. The processing circuitry may be configured to determine the one or more ERNA signals based on the determination that there is the change in the LFP measurements. That is, the change in the LFP measurements may trigger a measurement of the ERNA signals. In some examples, the processing circuitry may be configured to determine that there is the change in the LFP measurements during an instance where there is no delivery of therapeutic electrical stimulation signals. For instance, IMD 106 may not be delivering electrical stimulation signals, and during this time of non-delivery of the electrical stimulation signals, the processing circuitry may determine if the LFP changed. As there is no delivery of electrical stimulation signals, there may not be any ERNA signals.

In some examples, the processing circuitry may determine that there is no change (e.g., any change is less than a threshold signal level) in the LFP measurements for a period of time. That is, the trend of the LFP measurements indicate that there is no change in the LFP measurements. In such examples, the processing circuitry may be configured to determine the one or more ERNA signals based on the determination that there is no change in the LFP measurements for the period of time. For instance, because there is a lack of change in the LFP measurements, there may be uncertainty as to whether the patient is receiving therapeutic relief. In this case, the processing circuitry may utilize the ERNA signals to determine if a change in the parameters is needed. For instance, if the ERNA signals indicate that there is not sufficient therapeutic benefit, the processing circuitry may update the parameters.

As another example, the processing circuitry may be configured to determine that the one or more LFP measurements are greater than or below a threshold signal level for a period of time. In such examples, the processing circuitry may be configured to determine the one or more ERNA signals based on the determination that the one or more LFP measurements are greater than or below the threshold signal level for the period of time.

In some examples, the processing circuitry may determine that there is relatively low confidence in the LFP measurements. For instance, the processing circuitry may determine that there are artifacts in the LFP measurements (e.g., cardiac artifacts). The amplitude of the LFP measurements tends to be relatively low, while the amplitude of cardiac signals such as ECG tend to be much higher. If the processing circuitry determines that the amplitude of the sensed LFP measurements includes signal components having relatively high amplitude, the processing circuitry may determine that there is low confidence in the LFP measurements because the LFP measurements may be corrupted by cardiac artifacts. In this way, the processing circuitry may utilize the ERNA signals for updating the therapy parameters. This is another example way in which the processing circuitry may determine a set of one or more parameters for a set of one or more therapeutic electrical stimulation signals based on the one or more ERNA signals and the one or more LFP measurements. That is, the processing circuitry may determine that the one or more LFP measurements have low confidence (e.g., due to artifacts), and based on the determination, utilize ERNA signals for updating parameters.

In another example way to determine low confidence in the LFP measurements, the processing circuitry may determine that the LFP measurements are dominated by signal content in an undesired frequency band. For instance, there may be more signal content in a frequency band of less interest, than in a frequency band of interest. One cause for having signal content in the frequency band of less interest could be side effects. In such cases, the LFP measurements may be not provide as much information about effectiveness of therapy. The processing circuitry of IMD 106 may then utilize the ERNA signals for updating the parameters. This is another example way in which the processing circuitry may determine a set of one or more parameters for a set of one or more therapeutic electrical stimulation signals based on the one or more ERNA signals and the one or more LFP measurements. That is, the processing circuitry may determine that the one or more LFP measurements have low confidence (e.g., are not of interest), and based on the determination, utilize ERNA signals for updating parameters.

For example, for LFP, the processing circuitry may track power in a particular frequency band, and update parameters based on the power relative to a threshold signal level. The amplitude of the LFP measurements may be in the uV range, and may be dependent on the electrode arrangement used to detect the LFP. The relative low amplitude and frequency of these LFP measurements may cause the processing circuitry to analysis the LFP measurements the frequency domain. As an example, the processing circuitry may track one or more peaks in the frequency domain.

In some examples, if the LFP power exceeds threshold signal level for an extended time and is not responding to changes in applied stimulation, the processing circuitry may utilize ERNA signals to determine updates to the parameters. In some examples, the LFP amplitude may have been well below a threshold signal level for a time interval, and the processing circuitry may use an ERNA signal to determine that stimulation can be turned off for a time. As additional examples, the processing circuitry may utilize the ERNA signals during stimulation cycling to determine a shift in brain state that the processing circuitry confirms with LFP measurements. The processing circuitry may update parameters, such as duty cycle, restart stimulation, or terminal stimulation.

Accordingly, in some examples, the processing circuitry may determine that the one or more LFP measurements include artifacts. In such examples, the processing circuitry may determine the one or more ERNA signals based on the determination that the one or more LFP measurements include artifacts.

Although the above example describes artifacts and side effects impacting the LFP measurements, and the ERNA signals are utilized, the example techniques are not so limited. In some examples, the artifacts and/or side effects may impact the ERNA signals, and the processing circuitry may utilize the LFP measurements for determining updates to the parameters.

In the above example, a determination of the ERNA signals is triggered based on one or more LFP measurements. However, the example techniques are not so limited. In some examples, the ERNA signals may trigger determination of the LFP measurements. For example, the processing circuitry may determine whether to determine the one or more LFP measurements of the LFP based on the one or more ERNA signals, and determine the one or more LFP measurements of the LFP based on the determination the one or more LFP measurements are to be determined. For example, in response to determining that the one or more LFP measurements are to be determined, determine the one or more LFP measurements.

The examples above are described with respect to ERNA signals for ease. However, the example techniques may be applicable to evoked signals, of which an ERNA signal is an example.

In general, there may be benefits in using both the LFP measurements and the evoked signals for determining updates to the parameters for therapeutic electrical stimulation signals. For example, using only one of LFP measurements or the evoked signals to determine a patient state (e.g., whether the patient is receiving therapeutic relief, whether the medication is sufficiently effective, whether there should be change in therapy based on movement, etc.) may be insufficient. There may not be sufficient confidence that just the LFP measurements or the evoked signals can completely indicate if parameter updates are needed. By utilizing both the LFP measurements and the evoked signals, there may be higher likelihood of accurately determining if updates to the parameters is appropriate, and if so, by how much. That is, there may be more confidence in the determination that updates to the parameters is appropriate, and if updates are appropriate, more confidence that the updates provide therapeutic relief.

As an example, it may be possible that the evoked signals can be mapped to multiple different brain states, and LFP measurements can be mapped to multiple different brain states. The brain state may indicate the condition of the brain (e.g., whether patient 112 is receiving therapeutic relief). Therefore, having just the evoked signals or the LFP measurements may be insufficient to properly determine the patient condition. In some examples, by utilizing both evoked signals and LFP measurements, there may be more certainty in determining patient condition.

As an example of brain state, the brain state could be a state in which LFP signals are suppressed due to anesthesia, sleeping, active or inactive, but evoked signals are still present and used to confirm that sufficient stimulation is available. As another example, the LFP signal may be present without stimulation but there may be not evoked signal because there is not stimulation. However, the LFP may not be present when stimulation is present because the stimulation suppresses the LFP, but the evoked signal may be present because of stimulation. The brain state may indicate whether LFPs are present, but no evoked signal, or vice-versa. Accordingly, by having both LFP measurements and evoked signals, there may be more information available to properly determine whether the patient is receiving adequate therapy.

There may be various example ways in which the processing circuitry may determine updated parameters. That is, the processing circuitry may have caused the stimulation generation circuitry to deliver a first set of one or more therapeutic electrical stimulation signals according to a first set of one or more parameters. The processing circuitry may then determine a second set of one or more parameters for a second set of one or more therapeutic electrical stimulation signals based on the one or more ERNA signals and the one or more LFP measurements. For instance, the second set of one or more parameters may be updates to the first set of one or more parameters.

As one example, IMD 106 may store look-up table(s) that include information indicative of parameters for therapeutic electrical stimulation signals based on an amount of deviation of the LFP measurements from target LFP measurement or deviation of the ERNA signals from target ERNA signals. The processing circuitry may access the look-up table(s) and, based on the amount of deviation of the LFP measurement from the target LFP measurements and/or deviation of the ERNA signals from the target ERNA signals, determine the second set of one or more parameters for the second set of the one or more therapeutic electrical stimulation signals.

As another example, the processing circuitry may update the parameters by a certain amount to generate a first updated set of parameters, and cause the stimulation generation circuitry to deliver therapeutic electrical stimulation signals according to the first updated set of parameters. The processing circuitry may then determine the LFP measurements and/or ERNA signals (e.g., by delivering electrical stimulation signals that evoke the ERNA). The processing circuitry may compare the LFP measurements and/or ERNA signals to the target LFP measurements and/or ERNA signals. If the LFP measurements and/or ERNA signals are approximately equal to the target LFP measurements and/or ERNA signals (e.g., within a threshold signal level), then the processing circuitry may determine that the second set of one or more parameters are equal to the first updated set of parameters.

If the LFP measurements and/or ERNA signals deviate more than the threshold signal level from the target LFP measurements and/or ERNA signals, then the processing circuitry may update the first updated set of parameters to a second updated set of parameters. The processing circuitry may repeat the above example operations until the resulting LFP measurements and/or ERNA signals are approximately equal to the target LFP measurements and/or ERNA signals. Again, as described above, the target LFP measurements and/or ERNA signals may be previous LFP measurements and/or ERNA signals or a template LFP measurements and/or ERNA signals (e.g., desired amplitude of ERNA signals, desired resonance, desired number of peaks, etc.).

In the above examples, the LFP measurements and ERNA signals may be used to determine whether to update parameters and, in some examples, by how much. In some examples, in addition to or instead of updating parameters, the processing circuitry of IMD 106 may be configured to trigger alerts to patient 112 or a physician for changes in the LFP measurements and/or ERNA signals, trigger more detailed data collection or event recording based on the LFP measurements and/or ERNA signals, or perform other actions. In some instances, the patient themselves may use patient controller 104 to self-identify beneficial brain states based on their own perception of the therapeutic benefit of the stimulation.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. For example, the target tissue site may be the location of the signal source that generates the LFP having a signal component in the beta frequency band. The stimulation electrodes used to deliver stimulation to the target tissue site may be those that are most proximal to the signal source, e.g., as determined by the electrodes having the highest CSD, RMS, peak value, rectified average value, etc. Other lead 114 and IMD 106 implant sites are contemplated. For example, IMD 106 may be implanted on or within cranium 122, in some examples. Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. For example, one or more electrodes 116, 118 may be circumferentially-segmented DBS arrays of electrodes, and one or more electrodes 116, 118 may be non-segmented electrodes such as ring electrodes, as described above. In some examples, electrodes 116, 118 may only be circumferentially-segmented DBS arrays of electrodes, and in some examples, electrodes 116, 118 may only be non-segmented electrodes, such as ring electrodes.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. For example, as described above, the processing circuitry of IMD 106 may determine updates to parameters for the therapeutic electrical stimulation signal based on the respective LFP measurements and ERNA signals. In some examples, IMD 106 may output information indicative of the determined updated parameters for clinician approval. After approval, the processing circuitry of IMD 106 may store in a therapy program the determined parameter and may be configured to cause stimulation generation circuitry of IMD 106 to deliver the therapeutic electrical stimulation signal based on the determined parameters (e.g., by the processing circuitry selecting the therapy program that includes the determined parameters).

That is, the stimulation generation circuitry of IMD 106 may deliver a first set of one or more therapeutic electrical stimulation signals according to a first set of one or more parameters. Then, the processing circuitry may determine a second set of one or more parameters for a second set of one or more therapeutic electrical stimulation signals based on the one or more ERNA signals and the one or more LFP measurements, and cause the stimulation generation circuitry to deliver the second set of the one or more therapeutic electrical stimulation signals. The second set of one or more parameters may be updates to the first set of one or more parameters.

The delivery of the first set of one or more therapeutic electrical stimulation signals may not be necessary in all cases. For instance, memory of IMD 106 or some other memory may store the first set of one or more parameters for the first set of one or more therapeutic electrical stimulations signals. The processing circuitry may periodically update the first set of one or more parameters to the second set of one or more parameters based on both LFP measurements and ERNA signals, as described in this disclosure.

In some examples, clinician approval may not be necessary, such as in examples where the determined parameters for the therapeutic electrical stimulation signal are within a "safe-range" as assigned by the surgeon/clinician. In such examples, the processing circuitry of IMD 106 may output information indicative of the determined parameters for storage as a therapy program, and the stimulation generation circuitry may deliver the therapeutic electrical stimulation signal based on the determined parameters (e.g., by processing circuitry selecting the therapy program that includes the determined parameters). In this way, IMD 106 may generate therapeutic electrical stimulation based on the parameters of the selected therapy program to manage the patient symptoms associated with the patient disorder.

Rather than or in addition to using therapy programs, in some examples, it may be possible for the processing circuitry to directly output the information indicative of the determined parameters to the stimulation generation circuitry. Accordingly, there may be various way in which the processing circuitry may output information indicative of the determined parameters, such as to an external device like external programmer 104, described, below, to a therapy program, or to the stimulation generation circuitry.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). In some examples, ERNA signals may be used to evaluate the efficacy of the specific program being evaluated (e.g., certain resonant activity in the ERNA signal may be indicative of efficacious therapy). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

The above examples for determining whether to update parameters for therapeutic electrical stimulation, and if so, by how much were described with respect to the processing circuitry of IMD 106. In some examples, the processing circuitry of external programmer 104 may perform various techniques described above with respect to the processing circuitry of IMD 106.

For instance, the processing circuitry of programmer 104 may determine LFP measurements of an LFP (e.g., based on information transmitted by IMD 106). The processing circuitry of programmer 104 may cause the stimulation generation circuitry to deliver one or more electrical stimulation signals, and determine one or more ERNA signals that are evoked by delivery of respective ones of the one or more electrical stimulation signals (e.g., based on information transmitted by IMD 106). The processing circuitry of programmer 104 may determine a second set of one or more parameters for a second set of one or more therapeutic electrical stimulation signals based on the one or more ERNA signals and the one or more LFP measurements (e.g., based on look-up tables or based on titrating the parameters), and cause the stimulation generation circuitry to deliver the second set of the one or more therapeutic electrical stimulation signals.

Moreover, in some examples, the example techniques may be performed in the "cloud." For example, IMD 106 and/or programmer 104 may upload the LFP measurements and ERNA signals to one or more servers that form a cloud computing environment. Processing circuitry of the cloud computing environment may perform the example techniques described in this disclosure. Accordingly, in this disclosure, the processing circuitry that is configured to perform the example techniques may be any one or combination of the processing circuitry of IMD 106, the processing circuitry of programmer 104, and/or processing circuitry of a cloud computing environment.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder.

Figure 2:
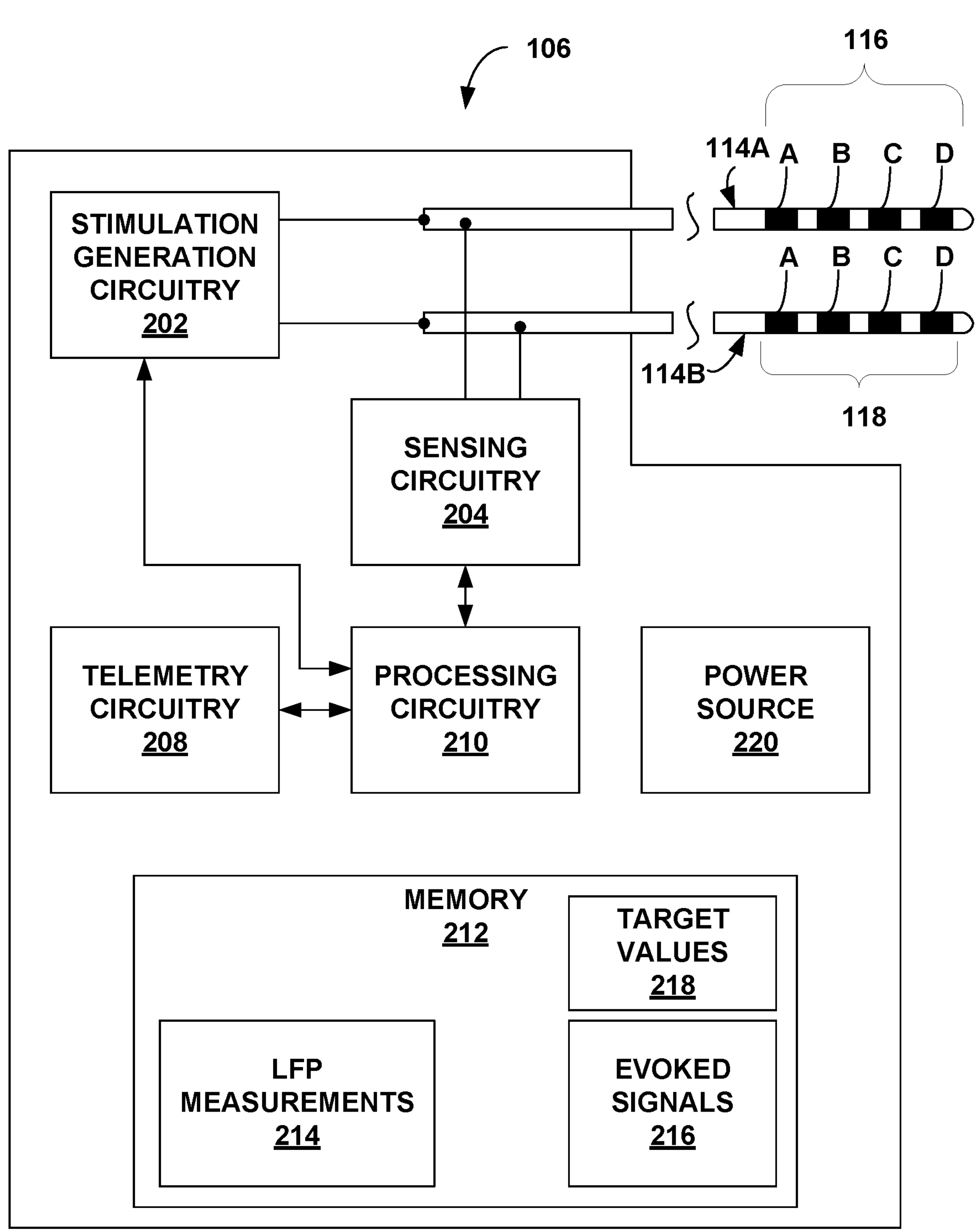
FIG. 2 is a block diagram of the example IMD of FIG. 1 for delivering DBS therapy according to an example of the techniques of the disclosure.

FIG. 2 is a block diagram of the example IMD 106 of FIG. 1 for delivering deep brain stimulation therapy. In the example shown in FIG. 2, IMD 106 includes processing circuitry 210, memory 212, stimulation generation circuitry 202, sensing circuitry 204, telemetry circuitry 208, and power source 220. Each of these circuits may be or include electrical circuitry configured to perform the functions attributed to each respective circuit. Memory 212 may include any volatile or non-volatile media, such as a random-access memory (RAM), read only memory (ROM), non-volatile RAM (NVRAM), electrically erasable programmable ROM (EEPROM), flash memory, and the like. Memory 212 may store computer-readable instructions that, when executed by processing circuitry 210, cause IMD 106 to perform various functions. Memory 212 may be a storage device or other non-transitory medium.

In the example shown in FIG. 2, memory 212 stores LFP measurements 214 and evoked signals 216. LFP measurements 214 may be the plurality of local field potential LFP measurements of an LFP that processing circuitry 210 receives. In some examples, evoked signals 216 may be ERNA signals. As described, the LFP is intrinsically generated by a signal source within brain 120 of patient 122. Evoked signals 216 may be information indicative of the ERNA signals that are evoked by delivery of the respective plurality of stimulation signals that IMD 106 delivers for evoking the respective ERNA signals. In one or more examples, processing circuitry 210 may utilize both LFP measurements 214 and evoked signals 216 to determine parameters for therapeutic electrical stimulation signals.

Stimulation generation circuitry 202, under the control of processing circuitry 210, generates stimulation signals (e.g., electrical stimulation signals for evoking ERNA signals and/or therapeutic electrical stimulation signals for delivering therapy) for delivery to patient 112 via selected combinations of electrodes 116, 118. An example range of electrical parameters believed to be effective in DBS to manage a movement disorder of patient include:

1. Pulse Rate, i.e., Frequency: between approximately 5 Hertz and approximately 500 Hertz, such as between approximately 5 to 220 Hertz or such as approximately 130 Hertz.
2. In the case of a voltage controlled system, Voltage Amplitude: between approximately 0.1 volts and approximately 50 volts, such as between approximately 2 volts and approximately 3 volts.
3. In the case of a current controlled system, Current Amplitude: between approximately 1 milliamps to approximately 3.5 milliamps, such as between approximately 1.0 milliamps and approximately 1.75 milliamps.
4. Pulse Width: between approximately 20 microseconds and approximately 500 microseconds, such as between approximately 50 microseconds and approximately 200 microseconds.

Accordingly, in some examples, stimulation generation circuitry 202 generates therapeutic electrical stimulation signals in accordance with the electrical parameters noted above. For example, processing circuitry 210 may utilize the example techniques described in this disclosure to determine the parameters for the therapeutic electrical stimulation signals (e.g., based on evaluation of LFP measurements 214 and evoked signals 216), and stimulation generation circuitry 202 may deliver the therapeutic electrical stimulation signals. Other ranges of therapy parameter values may also be useful, and may depend on the target stimulation site within patient 112. While stimulation pulses are described, stimulation signals may be of any form, such as continuous-time signals (e.g., sine waves) or the like.

In addition to delivering therapeutic electrical stimulation signals, stimulation generation circuitry 202 may be configured to deliver electrical stimulation signals for evoking ERNA signals (e.g., where information indicative of the ERNA signals are stored as evoked signals 216). Example parameters of the electrical stimulation signals for evoking ERNA signals include amplitude within range of 0 to 7.5 mA, such as 0 to 5 mA, frequency within range of 5 Hz to 250 Hz, such as 80 to 220 Hz, and pulse width in range of 20 to 450 microseconds, such as 60 to 120 microseconds. Again, ERNA signals are provided as an example, and should not be considered limiting.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs stored in memory 212 to apply particular parameter values specified by one or more of programs, such as voltage amplitude or current amplitude, pulse width, and/or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls stimulation generation circuitry 202 to generate and apply the stimulation signals to selected combinations of electrodes 116, 18. Stimulation generation circuitry 202 includes a plurality of pairs of voltage sources, current sources, voltage sinks, or current sinks connected to each of electrodes 116, 118 such that each pair of electrodes has a unique signal circuit. In other words, in these examples, each of electrodes 116, 118 is independently controlled via its own signal circuit (e.g., via a combination of a regulated voltage source and sink or regulated current source and sink), as opposed to switching signals between electrodes 116, 118.

Sensing circuitry 204 is configured to monitor signals from any combination of electrodes 116, 118. Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques.

Figure 4:
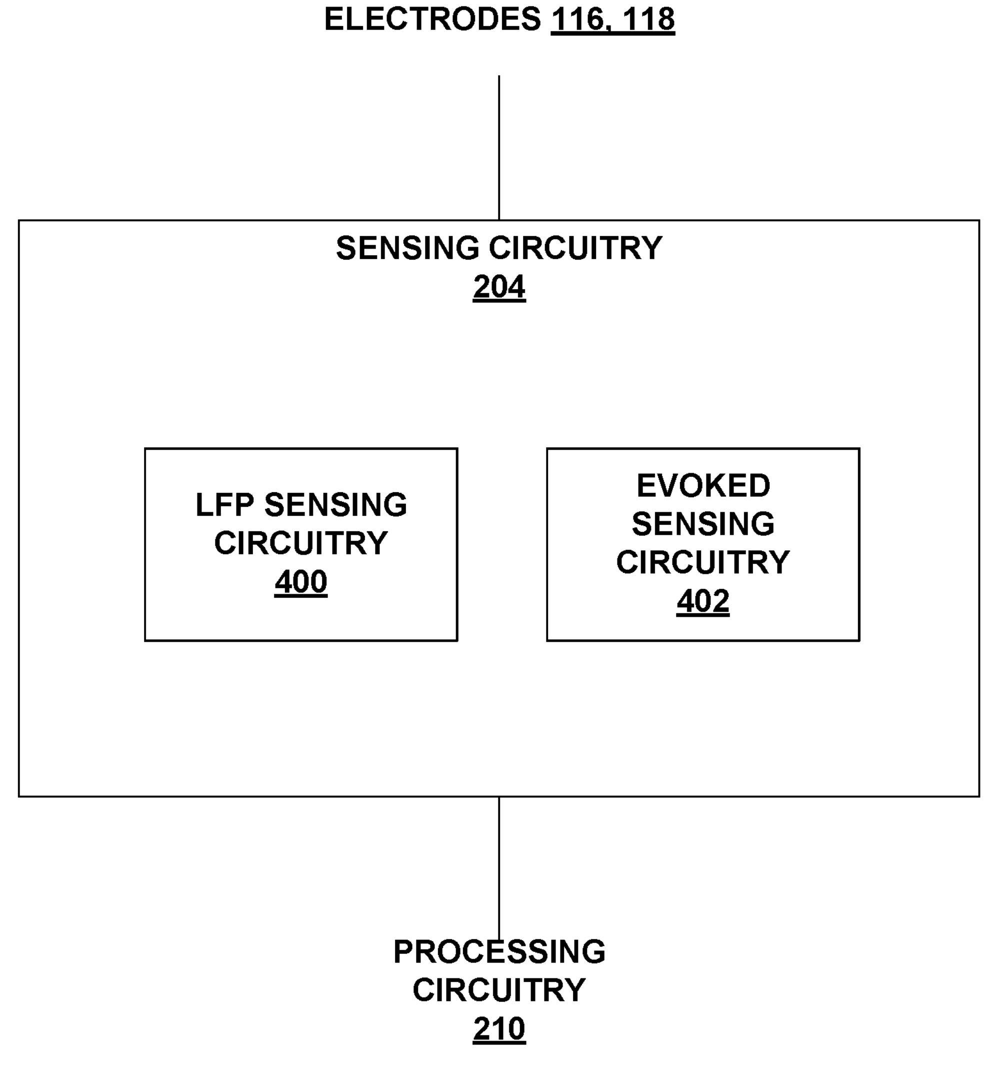
FIG. 4 is a block diagram illustrating an example of a sensing circuitry of FIG. 2 in further detail.

In some examples, sensing circuitry 204 includes one or more amplifiers, filters, and analog-to-digital converters. Sensing circuitry 204 may be used to sense physiological signals, such as LFP measurements for storage as LFP measurements 214 and evoked signals (e.g., ERNA signals) for storage as evoked signals 216. In some examples, sensing circuitry 204 measures LFP and ERNA signals from a particular combination of electrodes 116, 118. In some cases, the particular combination of electrodes for sensing includes different electrodes than a set of electrodes 116, 118 used to deliver electrical stimulation signals (e.g., therapeutic electrical stimulation signals or electrical stimulation signals for evoking ERNA signals). Alternatively, in other cases, the particular combination of electrodes used for sensing includes at least one of the same electrodes as a set of electrodes used to deliver stimulation signals to patient 120. Sensing circuitry 204 may provide signals to an analog-to-digital converter, for conversion into a digital signal for processing, analysis, storage, or output by processing circuitry 210. An example of sensing circuitry 204 is illustrated in FIG. 4.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations.

As an example, one or both of leads 114 may include circumferentially-segmented DBS arrays of electrodes and non-segmented electrodes (e.g., ring electrodes). As one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B.

The above is one example of the array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to stimulation generation circuitry 202 and sensing circuitry 204 via respective wires that are straight or coiled within the housing of the lead and run to a connector at the proximal end of the lead. In another example, each of the electrodes 116, 118 of the leads 114 may be electrodes deposited on a thin film. The thin film may include an electrically conductive trace for each electrode that runs the length of the thin film to a proximal end connector. The thin film may then be wrapped (e.g., a helical wrap) around an internal member to form the leads 114. These and other constructions may be used to create a lead with a complex electrode geometry.

Telemetry circuitry 208 supports wireless communication between IMD 106 and an external programmer 104 or another computing device under the control of processing circuitry 210. Processing circuitry 210 of IMD 106 may receive, as updates to programs, values for various parameters such as magnitude and electrode combination, from programmer 104 via telemetry circuitry 208. The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 104. In some examples, power requirements may be small enough to allow IMD 104 to utilize patient motion and implement a kinetic energy-scavenging device to trickle charge a rechargeable battery. In other examples, traditional batteries may be used for a limited period of time.

The DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers DBS to patient 120 and may adjust one or more parameters defining the electrical stimulation based on corresponding parameters of the sensed one or more signals of brain 120.

In some examples, processing circuitry 210 continuously measures the one or more LFP in real time. In other examples, processing circuitry 210 periodically samples the one or more LFP according to a predetermined frequency or after a predetermined amount of time. In some examples, processing circuitry 210 periodically samples the signal at a frequency of approximately 150 Hertz. In some examples, processing circuitry 210 may determine ERNA signals periodically, or according to a predetermined schedule.

For instance, in some examples, processing circuitry 210 may determine LFP measurements 214, and based on the LFP measurements 214 determine whether to determine evoked signals 216. Then based on LFP measurements 214 and/or evoked signals 216, processing circuitry 210 may determine parameters for therapeutic electrical stimulation signals.

According to the techniques of the disclosure, processing circuitry 210 may cause stimulation generation circuitry 202 to deliver a first set of one or more therapeutic electrical stimulation signals according to a first set of one or more parameters. However, delivery of the first set of one or more therapeutic electrical stimulation signals is not needed in every example. Processing circuitry 210 may determine one or more LFP measurements 214 of an LFP. For instance, sensing circuitry 204 may sense the LFP measurements for storage in memory 212 as LFP measurements 214. Processing circuitry 210 may retrieve LFP measurements 214.

Processing circuitry 210 may also cause stimulation generation circuitry 202 to deliver one or more electrical stimulation signals, and determine one or more evoked signals 216 that are evoked by delivery of respective ones of the one or more electrical stimulation signals. For example, sensing circuitry 204 may sense the ERNA signal for storage in memory 212 as evoked signals 216. Processing circuitry 210 may retrieve evoked signals 216.

Processing circuitry 210 may determine a second set of one or more parameters for a second set of one or more therapeutic electrical stimulation signals based on the one or more ERNA signals and the one or more LFP measurements. The second set of one or more parameters may be updates to the first set of one or more parameters. Processing circuitry 210 may then cause stimulation generation circuitry 202 to deliver the second set of the one or more therapeutic electrical stimulation signals.

There may be various ways in which processing circuitry 210 may determine the second set of one or more parameters. For instance, memory 212 may store target values 218. Processing circuitry 210 may utilize target values 218 to determine the second set of one or more parameters. Examples of target values 218 include information indicative of one or more previous LFP measurements and/or ERNA signals.

For example, target values 218 may include information such as peak amplitude, latency, number of peaks in ERNA signal, frequency of oscillation of ERNA signal, time between peaks of ERNA signal, etc. Target value 218 may include templates, as well. As described above, the templates may be based on LFP measurements and ERNA signals from a population of healthy individuals. In some examples, the templates may be based on LFP measurements and ERNA signals of patient 112 after patient 112 took medication to alleviate symptoms. In some examples, the templates may be based on LFP measurements and ERNA signals of patient 112 in different positions or movements. Another example of a template may be information indicative of a constant amplitude of the ERNA signals, desired amount of latency of peaks, timing between resonant peaks, number of peaks, etc.

Processing circuitry 210 may compare LFP measurements 214 and/or evoked signals 216 to target values 218 and based on the comparison update the first set of one or more parameters to determine the second set of one or more parameters. As one example, memory 212 may store a look-up table (not shown). The look-up table may store information indicative of an estimate of what the parameters should be given a difference between LFP measurements 214 and/or evoked signals 216 and target values 218. As another example, processing circuitry 210 may slightly update the first set of one or more parameters, and cause stimulation generation circuitry 202 to deliver electrical stimulation signals based on the slightly updated first set of one or more parameters. Processing circuitry 210 may re-determine LFP measurements 214 and evoked signals 216, compare the resulting LFP measurements 214 and evoked signals 216 to target values 218. Processing circuitry 210 may repeat such example operations until the LFP measurements 214 and/or evoked signals 216 are approximately equal to target values 218 (e.g., characteristics of LFP measurements 214 and evoked signals 216 are approximately same as characteristics defined by target values 218). The result may be the second set of one or more parameters.

As additional examples, processing circuitry 210 may utilize one of LFP measurements 214 or evoked signals 216 to determine whether to determine the other one of LFP measurements 214 or evoked signals 216. For ease of illustration, the example is described with utilizing LFP measurements 214 to determine whether to utilize evoked signals 216 for determining the second set of one or more parameters. However, using evoked signals 216 to determine whether to utilize LFP measurements 214 is also possible. Also, the using one of LFP measurements 214 to trigger the determination of evoked signals 216 for determining parameters for therapeutic electrical stimulation signals may be considered as determining a set of one or more parameters for a set of one or more therapeutic electrical stimulation signals based on the one or more ERNA signals and the one or more LFP measurements. This is because both the one or more ERNA signals and one or more LFP measurements are used to determine the parameters.

In some examples, sensing circuitry 204 may be configured to sense the one or more LFP measurements 214 during delivery of the first set of the one or more therapeutic electrical stimulation signals. That is, sensing circuitry 204 may be configured to sense for LFP signals even when therapeutic electrical stimulation signals are being delivered.

In one or more examples, generating evoked signals 216 may be based on stimulation generation circuitry 202 delivering electrical stimulation signals that evoke evoked signals 216. To cause stimulation generation circuitry 202 to deliver the one or more electrical stimulation signals (e.g., that evoke evoked signals 216), and to determine the one or more evoked signals 216, processing circuitry 210 may be configured to determine whether to cause stimulation generation circuitry 202 to deliver the one or more electrical stimulation signals and determine the one or more evoked signals 216 based on the one or more LFP measurements 214. That is, processing circuitry 210 may evaluate LFP measurements 214, and based on the evaluation of LFP measurements 214, processing circuitry 210 may determine whether or not to evoke evoked signals 216.

Processing circuitry 210 may cause stimulation generation circuitry 202 to deliver the one or more electrical stimulation signals and determine the one or more evoked signals 216 based on the determination that stimulation generation circuitry 202 is to deliver the one or more electrical stimulation signals. For instance, if based on the evaluation of LFP measurements 214, processing circuitry 210 determines that updates to one or more of the first set of parameters is not needed, then processing circuitry 210 may not utilize power delivering electrical stimulation signals to determine evoked signals 216. However, if based on the evaluation of LFP measurements 214, processing circuitry 210 determines that updates to one or more of the first set of parameters may be needed, then processing circuitry 210 may utilize power delivering electrical stimulation signals to evoke evoked signals 216.

As one example, to evaluate LFP measurements 214, processing circuitry 210 may retrieve from memory 212 information indicative of one or more target LFP measurements (e.g., as target values 218). Processing circuitry 210 may compare the one or more current LFP measurements to the one or more target LFP measurements, and determine whether to cause stimulation generation circuitry 202 to deliver the one or more electrical stimulation signals based on the comparison. For example, if LFP measurements 214 deviate by a threshold signal level from target values 218, then processing circuitry 210 may cause stimulation generation circuitry 202 to deliver electrical stimulation signals that evoke evoked signals 216. If, however, LFP measurements 214 do not deviate by the threshold signal level from target values 218, then processing circuitry 210 may not cause stimulation generation circuitry to deliver the electrical stimulation signals, and therefore, there may be no evoking of evoked signals 216.

As another example, processing circuitry 210 may determine that there is a change in the LFP measurements 214 (e.g., a first LFP measurement of LFP measurements 214 is different than a second LFP measurement of LFP measurements 214). Processing circuitry 210 may determine the one or more evoked signals 216 based on the determination that there is the change in the LFP measurements 214. Processing circuitry 210 may, in some cases, determine that there is the change in the LFP measurements 214 during an instance where there is no delivery of therapeutic electrical stimulation signals.

In some examples, processing circuitry 210 may determine that there is no change in the LFP measurements 214 for a period of time. That is, over a period of time, there is no change in each of LFP measurements 214 indicating a trend. Processing circuitry 210 may be configured to determine the one or more evoked signals 216 based on the determination that there is no change in the LFP measurements 214 for the period of time.

In some examples, processing circuitry 210 may determine that the one or more LFP measurements 214 are greater than or below a threshold signal level for a period of time. In such examples, processing circuitry 210 may determine the one or more ERNA signals based on the determination that the one or more LFP measurements are greater than or below the threshold signal level for the period of time. For instance, even if there is a change in the LFP measurements 214 over time, if the LFP measurements remain above or below a threshold signal level over a period of time, processing circuitry 210 may be triggered to determine one or more evoked signals 216.

As another example, processing circuitry 210 may determine that the one or more LFP measurements 214 include artifacts (e.g., based on amplitude, based on signal strength in undesired frequency bands, etc.). Processing circuitry 210 may determine the one or more evoked signals 216 based on the determination that the one or more LFP measurements 214 include artifacts. For instance, processing circuitry 210 may determine that there is low confidence in the use of LFP measurements 214 for determining whether to update the parameters, and in response, may determine one or more evoked signals 216 to use for updating the parameters.

Figure 3:
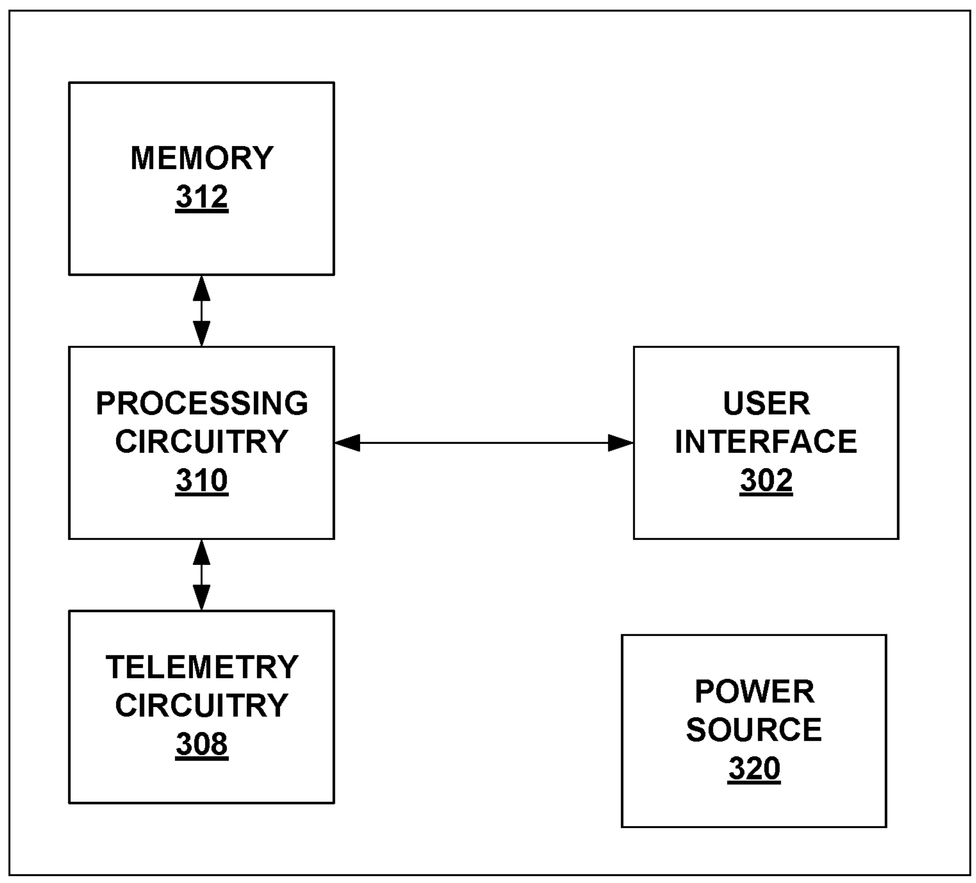
FIG. 3 is a block diagram of the external programmer of FIG. 1 for controlling delivery of DBS therapy according to an example of the techniques of the disclosure.

FIG. 3 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 312, user interface 302, telemetry circuitry 308, and power source 320. Memory 312 may store instructions that, when executed by processing circuitry 310, cause processing circuitry 310 and external programmer 104 to provide the functionality ascribed to external programmer 104 throughout this disclosure. Each of these components, or modules, may include electrical circuitry that is configured to perform some or all of the functionality described herein. For example, processing circuitry 310 may include processing circuitry configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 312, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate modules, in some examples, processing circuitry 310 and telemetry circuitry 308 may be functionally integrated with one another. In some examples, processing circuitry 310 and telemetry circuitry 308 correspond to individual hardware units, such as ASICs, DSPs, FPGAs, or other hardware units.

Memory 312 (e.g., a storage device) may store instructions that, when executed by processing circuitry 310, cause processing circuitry 310 and programmer 104 to provide the functionality ascribed to programmer 104 throughout this disclosure. For example, memory 312 may include instructions that cause processing circuitry 310 to obtain a parameter set from memory or receive a user input and send a corresponding command to IMD 106, or instructions for any other functionality. In addition, memory 312 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry circuitry 308 may support wireless communication between IMD 106 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 310 of external programmer 104 defines the parameters of electrical stimulation therapy, stored in memory 312, for delivering DB S to patient 120. In one example, processing circuitry 310 of external programmer 104, via telemetry circuitry 308, issues commands to IMD 106 causing IMD 106 to deliver electrical stimulation therapy via electrodes 116, 118 via leads 114.

In one or more examples, programmer 104 may be configured to perform one or more of the example techniques described in this disclosure. For instance, processing circuitry 310 may be configured to perform one or more of the example operations described above with respect to processing circuitry 210.

For example, processing circuitry 310 may be configured to cause stimulation generation circuitry 202 to deliver a first set of one or more therapeutic electrical stimulation signals according to a first set of one or more parameters. For instance, processing circuitry 310 may output the first set of one or more parameters to IMD 106 for storage, which stimulation generation circuitry 202 uses for delivery of the first set of one or more therapeutic electrical stimulation signals.

To determine one or more LFP measurements of an LFP, processing circuitry 310 may receive the LFP measurements from IMD 106. Also, processing circuitry 310 may output instructions that cause stimulation generation circuitry 202 to deliver one or more electrical stimulation signals. To determine one or more ERNA signals that are evoked by delivery of respective ones of the one or more electrical stimulation signals, processing circuitry 310 may receive information indicative of the ERNA signals from IMD 106. Processing circuitry 310 may determine a second set of one or more parameters for a second set of one or more therapeutic electrical stimulation signals based on the one or more ERNA signals and the one or more LFP measurements. Processing circuitry 310 may output the second set of one or more parameters to IMD 106, and cause stimulation generation circuitry 202 to deliver the second set of the one or more therapeutic electrical stimulation signals.

FIG. 4 is a block diagram illustrating an example of a sensing circuitry of FIG. 2 in further detail. As illustrated in FIG. 4, sensing circuitry 204 includes LFP sensing circuitry 400 and evoked sensing circuitry 402. LFP sensing circuitry 400 may be configured to specifically determine LFP measurements, and evoked sensing circuitry 402 may be configured to specifically sense evoked signals (e.g., ERNA signals).

For instance, an LFP can generally be measured at any time, including instances when IMD 106 is delivering electrical stimulation (e.g., therapeutic electrical stimulation signals or electrical stimulation signals that evoke ERNA signals). This is because the LFP is intrinsically generated by a signal source (e.g., one or more neurons) within brain 120 of patient 122. Accordingly, LFP sensing circuitry 400 may be configured to continuously determine LFP measurements, periodically determine LFP measurements, or determine LFP measurements in accordance with a schedule irrespective of when stimulation generation circuitry 202 is configured to deliver the stimulation (e.g., therapeutic electrical stimulation signals or electrical stimulation signals that evoke ERNA signals).

For example, as described above, processing circuitry 210 or 310 may cause stimulation generation circuitry 202 to deliver a first set of one or more therapeutic electrical stimulation signals according to a first set of one or more parameters. In some examples, processing circuitry 210 may determine the one or more LFP measurements during delivery of the first set of the one or more therapeutic electrical stimulation signals. LFP sensing circuitry 400 may sense the LFP measurements during delivery of the first set of one or more therapeutic electrical stimulation signals.

Evoked sensing circuitry 402 may, however, sense ERNA signals in response to delivery of an electrical stimulation signal. Accordingly, during the time the electrical stimulation signal is being delivered, and prior to the delivery of the electrical stimulation signal, evoked sensing circuitry 402 may be configured to not sense evoked signals.

Furthermore, in response to delivery of an electrical stimulation signal, the signal that sensing circuitry 204 senses may be a composite signal includes at least two components. The first component is the ERNA signal that is evoked due to the delivery of the electrical stimulation signal. The second component may be the LFP, which may still be present even with delivery of the electrical stimulation signal that evoked the ERNA signal because such electrical stimulation signal may not be therapeutic.

Accordingly, processing circuitry 210 may be configured to differentiate between the LFP measurement and the ERNA signal in such a composite signal. In some examples, LFP sensing circuitry 400 may be configured to filter out signals that are out of the frequency band of the LFP band of interest (e.g., outside of the beta band). Evoked sensing circuitry 402 may be similarly configured to filter out signals that are out of the frequency band of ERNA signals (e.g., filter out signals outside the 270 to 340 Hz range). Accordingly, processing circuitry 210 may receive the LFP measurements from LFP sensing circuitry 400 and the ERNA signals from evoked sensing circuitry 402.

The example of sensing circuitry 204 of FIG. 4 is one example, and should not be considered limiting. In some examples, sensing circuitry 204 may not necessarily include LFP sensing circuitry 400 and evoked sensing circuitry 402. In such examples, processing circuitry 210 may receive the composite signal that includes both the LFP and the ERNA signals, when an electrical stimulation signal that evokes ERNA signals is delivered by stimulation generation circuitry 202. To differentiate between the ERNA signals and the LFP, processing circuitry 210 may be configured to determine the LFP measurement immediately before stimulation generation circuitry 202 delivers electrical stimulation that evokes an ERNA signal. Then, when processing circuitry 210 receive the composite signal that includes the LFP and the ERNA signal, processing circuitry 210 may subtract the LFP measurement taken immediately before stimulation circuitry 202 delivered electrical stimulation that evoked the ERNA signal from the composite signal to determine the ERNA signal.

Figure 5:
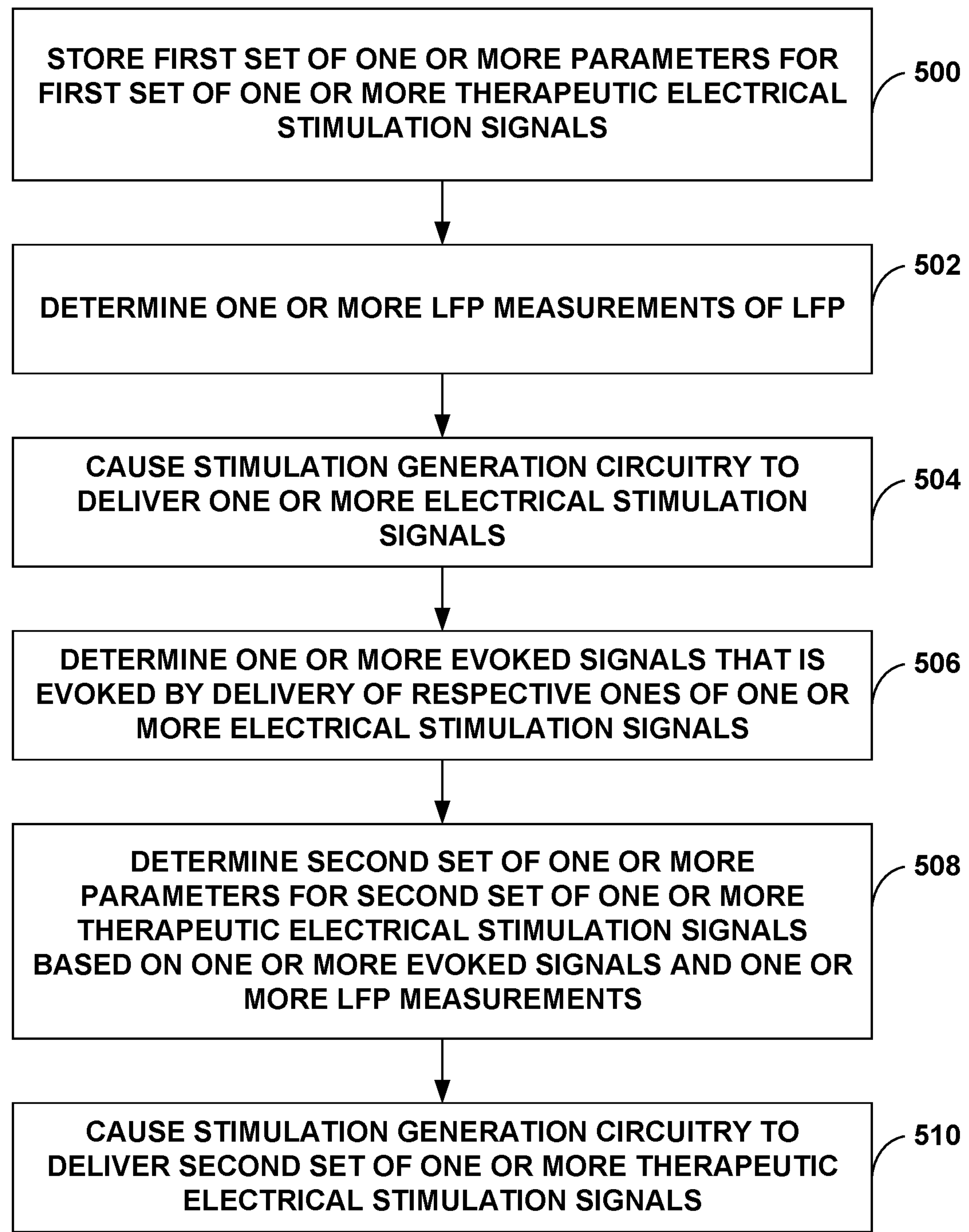
FIG. 5 is a flowchart illustrating an example operation in accordance with techniques of the disclosure.

FIG. 5 is a flowchart illustrating an example operation in accordance with techniques of the disclosure. The example of FIG. 5 is described with respect to processing circuitry. Examples of the processing circuitry includes processing circuitry 210 of IMD 106, processing circuitry 310 of programmer 104, processing circuitry of a cloud computing environment, or any combination thereof. For example, the processing circuitry configured to perform the example operations described for FIG. 5 may be part of IMD 106, programmer 104, or is part of IMD 106, programmer 104, or both IMD 106 and the programmer 104.

The processing circuitry may be configured to store a first set of one or more parameters for a first set of one or more therapeutic electrical stimulation signals (500). The first set of one or more parameters may be parameters that the clinician determined as part of determining initial parameters. In some examples, the first set of one or more parameters may be parameters that were updated, but are due for further updating.

For instance, as described above, due to changes in patient condition (e.g., worsening of patient condition or improvements in patient condition) or due to lead migration, there may be instances to update the parameters. This disclosure describes use of LFP measurements and evoked signals (e.g., ERNA signals) to determine the updates to the parameters in a closed-loop manner, which may result in possibly more accurate parameters with less time spent in determining the parameters.

In accordance with one or more examples described in this disclosure, the processing circuitry may determine one or more LFP measurements of an LFP, where the LFP is intrinsically generated by a signal source within a brain of the patient (502). For example, LFP sensing circuitry 400 may sensing the LFP measurements, and store the LFP measurements as LFP measurements 214 in memory 212. The processing circuitry may retrieve LFP measurements 214 from memory 212 to determine the one or more LFP measurements.

The processing circuitry may be configured to determine one or more evoked signals. As described above and in more detail with respect to FIG. 6, in some examples, the processing circuitry may determine one or more evoked signals based on evaluation of LFP measurements 214. However, the example techniques are not so limited. In some examples, the processing circuitry may determine the one or more evoked signals regardless of the LFP measurements. In some examples, the processing circuitry may skip determination of the LFP measurements, and instead first determine the one or more evoked signals. Based on the one or more evoked signals, the processing circuitry may determine whether or not to determine the LFP measurements.

To determine the one or more evoked signals, the processing circuitry may cause the stimulation generation circuitry 202 to deliver one or more electrical stimulation signals (504). The processing circuitry may determine one or more evoked signals that are evoked by delivery of respective ones of the one or more electrical stimulation signals (506). For example, evoked sensing circuitry 402 may sense the evoked signals and store the evoked signals as evoked signals 216 in memory 212. The processing circuitry may retrieve evoked signals 216 from memory 212 to determine the one or more evoked signals.

Evoked signals can be in the 10-100s of uV range, but depends on the arrangement of electrodes. Frequency content is in the 100s of Hz, such as between approximately 100 Hz and less than 1000 Hz in one example. For LFP, frequency content is usually less than 100 Hz but does not preclude the existence of intrinsic activity that occurs above that 100 Hz.

The processing circuitry may determine a second set of one or more parameters for a second set of one or more therapeutic electrical stimulation signals based on the one or more evoked signals and the one or more LFP measurements (508). The second set of one or more parameters may be updates to the first set of one or more parameters. As one example, the processing circuitry may compare one or more both of LFP measurements 214 and evoked signals 216 to target values 218 and determine the second set of one or more parameters based on the comparison. For instance, the processing circuitry may titrate the one or more parameters until the LFP measurements 214 and evoked signals 216 are approximately equal to target values 218 as a way to determine the second set of one or more parameters for the second set of one or more therapeutic electrical stimulation signals.

The processing circuitry may cause stimulation generation circuitry 202 to deliver the second set of the one or more therapeutic electrical stimulation signals (510). In this way, the processing circuitry may deliver therapeutic electrical stimulation signals having updated parameters, where the updating of the parameters is performed in a closed-loop manner using both the LFP measurements and the evoked signals.

Figure 6:
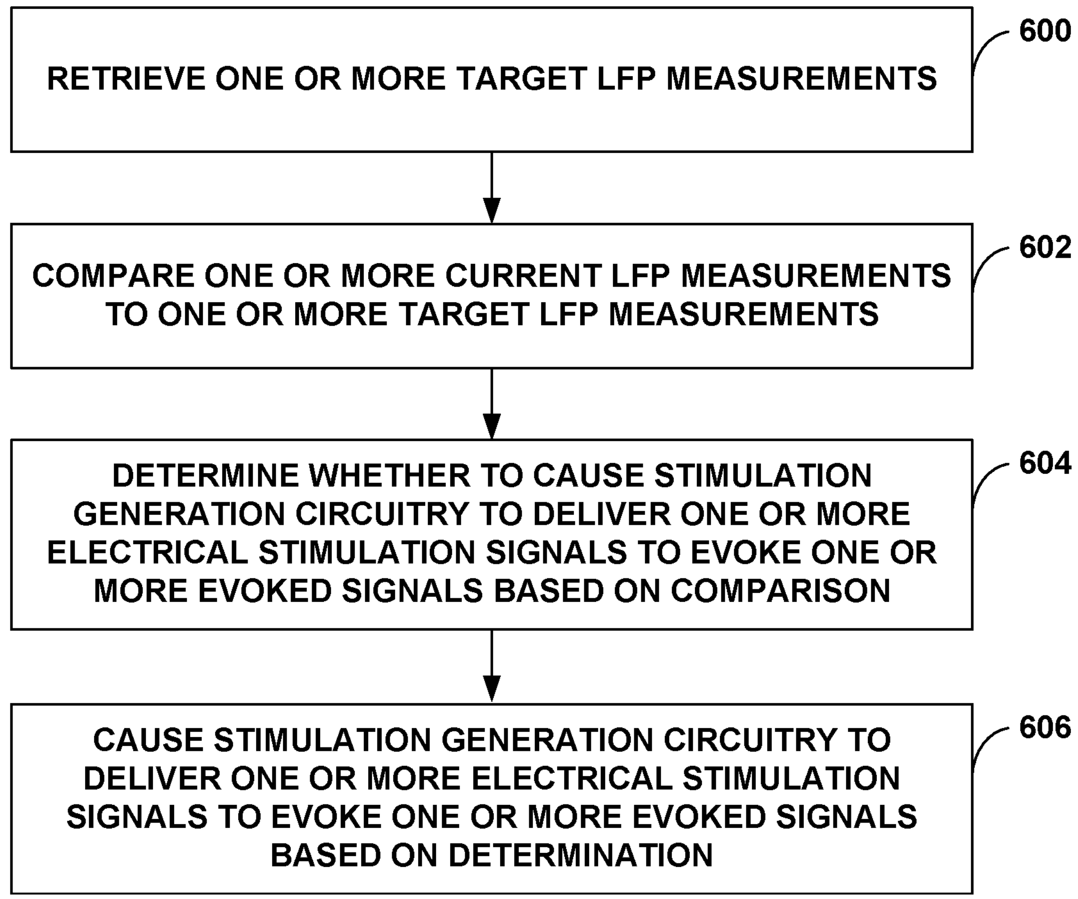
FIG. 6 is another flowchart illustrating an example operation in accordance with techniques of the disclosure.

FIG. 6 is another flowchart illustrating an example operation in accordance with techniques of the disclosure. The example of FIG. 6 is described with respect to processing circuitry. Examples of the processing circuitry includes processing circuitry 210 of IMD 106, processing circuitry 310 of programmer 104, processing circuitry of a cloud computing environment, or any combination thereof. For example, the processing circuitry configured to perform the example operations described for FIG. 6 may be part of IMD 106, programmer 104, or is part of IMD 106, programmer 104, or both IMD 106 and the programmer 104.

In some examples, as described in FIG. 5, the processing circuitry may determine one or more LFP measurements, and may selectively determine the one or more evoked signals based on evaluation of the one or more LFP measurements. For instance, the processing circuitry may retrieve one or more target LFP measurements (600). The one or more target LFP measurements may be part of target values 218.

The processing circuitry may compare the one or more current LFP measurements to one or more target LFP measurements (602). For instance, the processing circuitry may compare characteristics of the current LFP measurements with stored characteristics of the target LFP measurements.

The processing circuitry may determine whether to cause stimulation generation circuitry 202 to deliver one or more electrical stimulation signals to evoke one or more evoked signals based on the comparison (604). For example, if the processing circuitry determine that characteristics of the current LFP measurements do not sufficiently deviate from the target LFP measurements, then the processing circuitry may determine that no updates to the parameters is needed, and therefore, no need to determine one or more evoked signals for updating parameters. If, however, the processing circuitry determines that the characteristics of the current LFP measurements sufficiently deviate from the target LFP measurements, then the processing circuitry may determine that updates to the parameters is appropriate, and therefore, determine one or more evoked signals for updating parameters.

The processing circuitry may cause stimulation generation circuitry 202 to deliver one or more electrical stimulation signals to evoke one or more evoked signals based on the determination (606). For example, if there is sufficient deviation between current LFP measurements and target LFP measurements, then the processing circuitry cause stimulation generation circuitry 202 to deliver one or more electrical stimulation signals to evoke one or more evoked signals. If there is not sufficient deviation between the current LFP measurements and the target LFP measurements, then the processing circuitry may bypass causing stimulation generation circuitry 202 to deliver one or more electrical stimulation signals to evoke one or more evoked signals.

The following describes one or more examples that may be performed separately or in various combinations in accordance with techniques described in this disclosure.

Example 1. A system for closed-loop therapy, the system comprising: memory configured to store a first set of one or more parameters for a first set of one or more therapeutic electrical stimulation signals; and processing circuitry coupled to the memory and configured to: determine one or more local field potential (LFP) measurements of an LFP, wherein the LFP is intrinsically generated by a signal source within a brain of the patient; cause stimulation generation circuitry to deliver one or more electrical stimulation signals; determine one or more evoked resonant neural activity (ERNA) signals that are evoked by delivery of respective ones of the one or more electrical stimulation signals; determine a second set of one or more parameters for a second set of one or more therapeutic electrical stimulation signals based on the one or more ERNA signals and the one or more LFP measurements, wherein the second set of one or more parameters are updates to the first set of one or more parameters; and cause the stimulation generation circuitry to deliver the second set of the one or more therapeutic electrical stimulation signals.

Example 2. The system of example 1, wherein to determine the one or more LFP measurements, the processing circuitry is configured to determine that there is a change in the LFP measurements, and wherein to determine the one or more ERNA signals, the processing circuitry is configured to determine the one or more ERNA signals based on the determination that there is the change in the LFP measurements.

Example 3. The system of example 2, wherein the processing circuitry is configured to determine that there is the change in the LFP measurements during an instance where there is no delivery of therapeutic electrical stimulation signals.

Example 4. The system of example 1, wherein to determine the one or more LFP measurements, the processing circuitry is configured to determine that there is no change in the LFP measurements for a period of time, and wherein to determine the one or more ERNA signals, the processing circuitry is configured to determine the one or more ERNA signals based on the determination that there is no change in the LFP measurements for the period of time.

Example 5. The system of example 1, wherein to determine the one or more LFP measurements, the processing circuitry is configured to determine that the one or more LFP measurements are greater than or below a threshold for a period of time, and wherein to determine the one or more ERNA signals, the processing circuitry is configured to determine the one or more ERNA signals based on the determination that the one or more LFP measurements are greater than or below the threshold for the period of time.

Example 6. The system of any of examples 1-5, wherein the processing circuitry is configured to determine that the one or more LFP measurements include artifacts, and wherein to determine the one or more ERNA signals, the processing circuitry is configured to determine the one or more ERNA signals based on the determination that the one or more LFP measurements include artifacts.

Example 7. The system of any of examples 1-6, wherein the one or more LFP measurements comprise one or more current LFP measurements, wherein the processing circuitry is configured to retrieve from the memory information indicative of one or more target LFP measurements, and wherein to determine the one or more ERNA signals, the processing circuitry is configured to: compare the one or more current LFP measurements to the one or more target LFP measurements; and control, based on the comparison, the stimulation circuitry to deliver the one or more electrical stimulation signals.

Example 8. The system of any of examples 1-7, further comprising sensing circuitry configured to sense the one or more LFP measurements during delivery of the first set of the one or more therapeutic electrical stimulation signals.

Example 9. The system of example 1, wherein to determine the one or more LFP measurements of the LFP, the processing circuitry is configured to: determine whether to determine the one or more LFP measurements of the LFP based on the one or more ERNA signals; and in response to determining that the one or more LFP measurements are to be determined, determine the one or more LFP measurements.

Example 10. The system of any of examples 1-9, further comprising an implantable medical device (IMD), wherein the IMD includes the processing circuitry.

Example 11. The system of any of examples 1-9, further comprising a programmer, wherein the programmer includes the processing circuitry.

Example 12. The system of any of examples 1-9, further comprising an implantable medical device (IMD) and a programmer, and wherein the processing circuitry is part of the IMD, the programmer, or both the IMD and the programmer.

Example 13. A method for closed-loop therapy, the method comprising: storing a first set of one or more parameters for a first set of one or more therapeutic electrical stimulation signals; determining one or more local field potential (LFP) measurements of an LFP, wherein the LFP is intrinsically generated by a signal source within a brain of the patient; causing stimulation generation circuitry to deliver one or more electrical stimulation signals; determining one or more evoked resonant neural activity (ERNA) signals that are evoked by delivery of respective ones of the one or more electrical stimulation signals; determining a second set of one or more parameters for a second set of one or more therapeutic electrical stimulation signals based on the one or more ERNA signals and the one or more LFP measurements, wherein the second set of one or more parameters are updates to the first set of one or more parameters; and causing the stimulation generation circuitry to deliver the second set of the one or more therapeutic electrical stimulation signals.

Example 14. The method of example 13, wherein determining the one or more LFP measurements comprises determining that there is a change in the LFP measurements, and wherein determining the one or more ERNA signals comprises determining the one or more ERNA signals based on the determination that there is the change in the LFP measurements.

Example 15. The method of example 14, wherein determining that there is a change in the LFP measurements comprises determining that there is the change in the LFP measurements during an instance where there is no delivery of therapeutic electrical stimulation signals.

Example 16. The method of example 13, wherein determining the one or more LFP measurements comprises determining that there is no change in the LFP measurements for a period of time, and wherein determining the one or more ERNA signals comprises determining the one or more ERNA signals based on the determination that there is no change in the LFP measurements for the period of time.

Example 17. The method of example 13, wherein determining the one or more LFP measurements comprises determining that the one or more LFP measurements are greater than or below a threshold for a period of time, and determining the one or more ERNA signals comprises determining the one or more ERNA signals based on the determination that the one or more LFP measurements are greater than or below the threshold for the period of time.

Example 18. The method of any of examples 13-17, further comprising determining that the one or more LFP measurements include artifacts, and wherein determining the one or more ERNA signals comprises determining the one or more ERNA signals based on the determination that the one or more LFP measurements include artifacts.

Example 19. The method of any of examples 13-18, wherein the one or more LFP measurements comprise one or more current LFP measurements, the method further comprising retrieving from memory information indicative of one or more target LFP measurements, and wherein determining the one or more ERNA signals comprises: comparing the one or more current LFP measurements to the one or more target LFP measurements; and controlling, based on the comparison, the stimulation circuitry to deliver the one or more electrical stimulation signals.

Example 20. The method of any of examples 13-19, further comprising sensing the one or more LFP measurements during delivery of the first set of the one or more therapeutic electrical stimulation signals.

Example 21. The method of example 13, wherein determining the one or more LFP measurements of the LFP comprises: determining whether to determine the one or more LFP measurements of the LFP based on the one or more ERNA signals; and in response to determining that the one or more LFP measurements are to be determined, determining the one or more LFP measurements.

Example 22. A computer-readable storage medium storing instructions thereon that when executed cause one or more processors to: store a first set of one or more parameters for a first set of one or more therapeutic electrical stimulation signals; determine one or more local field potential (LFP) measurements of an LFP, wherein the LFP is intrinsically generated by a signal source within a brain of the patient; cause stimulation generation circuitry to deliver one or more electrical stimulation signals; determine one or more evoked resonant neural activity (ERNA) signals that are evoked by delivery of respective ones of the one or more electrical stimulation signals; determine a second set of one or more parameters for a second set of one or more therapeutic electrical stimulation signals based on the one or more ERNA signals and the one or more LFP measurements, wherein the second set of one or more parameters are updates to the first set of one or more parameters; and cause the stimulation generation circuitry to deliver the second set of the one or more therapeutic electrical stimulation signals.

Example 23. The computer-readable storage medium of example 22, further comprising instructions that cause the one or more processors to perform the method of any of examples 14-21.

Example 24. A system for closed-loop therapy, the system comprising: means for storing a first set of one or more parameters for a first set of one or more therapeutic electrical stimulation signals; means for determining one or more local field potential (LFP) measurements of an LFP, wherein the LFP is intrinsically generated by a signal source within a brain of the patient; means for causing stimulation generation circuitry to deliver one or more electrical stimulation signals; means for determining one or more evoked resonant neural activity (ERNA) signals that are evoked by delivery of respective ones of the one or more electrical stimulation signals; means for determining a second set of one or more parameters for a second set of one or more therapeutic electrical stimulation signals based on the one or more ERNA signals and the one or more LFP measurements, wherein the second set of one or more parameters are updates to the first set of one or more parameters; and means for causing the stimulation generation circuitry to deliver the second set of the one or more therapeutic electrical stimulation signals.

Example 25. The system of example 24, further comprising means for performing the method of any of examples 14-21.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A system for closed-loop therapy, the system comprising:

memory configured to store a first set of one or more parameters for a first set of one or more therapeutic electrical stimulation signals; and processing circuitry coupled to the memory and configured to:

determine one or more local field potential (LFP) measurements of an LFP, wherein the LFP is of a first signal type that is intrinsically generated by a signal source within a brain of a patient;

cause delivery of one or more electrical stimulation signals;

determine one or more evoked signals that are evoked by delivery of respective ones of the one or more electrical stimulation signals, wherein the one or more evoked signals are of a second signal type that is different than the first signal type of the LFP;

determine a second set of one or more parameters for a second set of one or more therapeutic electrical stimulation signals based on the one or more evoked signals having the second signal type and the one or more LFP measurements of the LFP having the first signal type, wherein the second set of one or more parameters are updates to the first set of one or more parameters; and cause delivery of the second set of the one or more therapeutic electrical stimulation signals.

2. The system of claim 1, wherein to determine the one or more LFP measurements, the processing circuitry is configured to determine that there is a change in the LFP measurements, and wherein to determine the one or more evoked signals, the processing circuitry is configured to determine the one or more evoked signals responsive to the determination that there is the change in the LFP measurements.

3. The system of claim 2, wherein the processing circuitry is configured to determine that there is the change in the LFP measurements during an instance where there is no delivery of therapeutic electrical stimulation signals.

4. The system of claim 1, wherein to determine the one or more LFP measurements, the processing circuitry is configured to determine that there is no change in the LFP measurements for a period of time, and wherein to determine the one or more evoked signals, the processing circuitry is configured to determine the one or more evoked signals responsive to the determination that there is no change in the LFP measurements for the period of time.

5. The system of claim 1, wherein to determine the one or more LFP measurements, the processing circuitry is configured to determine that the one or more LFP measurements are greater than or below a threshold signal level for a period of time, and wherein to determine the one or more evoked signals, the processing circuitry is configured to determine the one or more evoked signals responsive to the determination that the one or more LFP measurements are greater than or below the threshold signal level for the period of time.

6. The system of claim 1, wherein the processing circuitry is configured to determine that the one or more LFP measurements include artifacts, and wherein to determine the one or more evoked signals, the processing circuitry is configured to determine the one or more evoked signals responsive to the determination that the one or more LFP measurements include artifacts.

7. The system of claim 1, wherein the one or more LFP measurements comprise one or more current LFP measurements, wherein the processing circuitry is configured to retrieve from the memory information indicative of one or more target LFP measurements, and wherein to determine the one or more evoked signals, the processing circuitry is configured to:

compare the one or more current LFP measurements to the one or more target LFP measurements;

based on the one or more current LFP measurements deviating from the one or more target LFP by a threshold signal level, determine that the one or more evoked signals are to be determined; and determine the one or more evoked signal responsive to the determination that the one or more evoked signals are to be determined.

8. The system of claim 1, further comprising sensing circuitry configured to sense the one or more LFP measurements during delivery of the first set of the one or more therapeutic electrical stimulation signals.

9. The system of claim 1, wherein to determine the one or more LFP measurements of the LFP, the processing circuitry is configured to:

utilize the one or more evoked signals to determine whether to trigger a determination of the one or more LFP measurements of the LFP; and in response to determining to trigger the determination of the one or more LFP measurements of the LFP, determine the one or more LFP measurements.

10. The system of claim 1, further comprising an implantable medical device (IMD), wherein the IMD includes the processing circuitry.

11. The system of claim 1, further comprising a programmer, wherein the programmer includes the processing circuitry.

12. The system of claim 1, further comprising an implantable medical device (IMD) and a programmer, and wherein the processing circuitry is part of the IMD, the programmer, or both the IMD and the programmer.

13. The system of claim 1, wherein the one or more evoked signals are one or more evoked resonant neural activity signals.

14. A method for closed-loop therapy, the method comprising:

storing a first set of one or more parameters for a first set of one or more therapeutic electrical stimulation signals;

determining one or more local field potential (LFP) measurements of an LFP, wherein the LFP is of a first signal type that is intrinsically generated by a signal source within a brain of a patient;

causing delivery of one or more electrical stimulation signals;

determining one or more evoked signals that are evoked by delivery of respective ones of the one or more electrical stimulation signals, wherein the one or more evoked signals are of a second signal type that is different than the first signal type of the LFP;

determining a second set of one or more parameters for a second set of one or more therapeutic electrical stimulation signals based on the one or more evoked signals having the second signal type and the one or more LFP measurements of the LFP having the first signal type, wherein the second set of one or more parameters are updates to the first set of one or more parameters; and causing delivery of the second set of the one or more therapeutic electrical stimulation signals.

15. The system of claim 1, wherein a respective evoked signal of the one or more evoked signals is not present within the brain prior to delivery of a respective electrical stimulation signal that evoked the respective evoked signal.

16. The method of claim 14, wherein the one or more evoked signals are one or more evoked resonant neural activity signals.

17. The method of claim 14, wherein determining the one or more LFP measurements comprises determining that there is a change in the LFP measurements, and wherein determining the one or more evoked signals comprises determining the one or more evoked signals responsive to the determination that there is the change in the LFP measurements.

18. The method of claim 17, wherein determining that there is a change in the LFP measurements comprises determining that there is the change in the LFP measurements during an instance where there is no delivery of therapeutic electrical stimulation signals.

19. The method of claim 14, wherein determining the one or more LFP measurements comprises determining that there is no change in the LFP measurements for a period of time, and wherein determining the one or more evoked signals comprises determining the one or more evoked signals responsive to the determination that there is no change in the LFP measurements for the period of time.

20. The method of claim 14, wherein determining the one or more LFP measurements comprises determining that the one or more LFP measurements are greater than or below a threshold signal level for a period of time, and determining the one or more evoked signals comprises determining the one or more evoked signals responsive to the determination that the one or more LFP measurements are greater than or below the threshold signal level for the period of time.

21. The method of claim 14, further comprising determining that the one or more LFP measurements include artifacts, and wherein determining the one or more evoked signals comprises determining the one or more evoked signals responsive to the determination that the one or more LFP measurements include artifacts.

22. The method of claim 14, wherein the one or more LFP measurements comprise one or more current LFP measurements, the method further comprising retrieving from memory information indicative of one or more target LFP measurements, and wherein determining the one or more evoked signals comprises:

comparing the one or more current LFP measurements to the one or more target LFP measurements;

based on the one or more current LFP measurements deviating from the one or more target LFP by a threshold signal level, determining that the one or more evoked signals are to be determined; and determining the one or more evoked signal responsive to the determination that the one or more evoked signals are to be determined.

23. The method of claim 14, further comprising sensing the one or more LFP measurements during delivery of the first set of the one or more therapeutic electrical stimulation signals.

24. The method of claim 14, wherein determining the one or more LFP measurements of the LFP comprises:

utilizing the one or more evoked signals to determine whether to trigger a determination of the one or more LFP measurements of the LFP; and in response to determining to trigger the determination of the one or more LFP measurements of the LFP, determining the one or more LFP measurements.

25. A non-transitory computer-readable storage medium storing instructions thereon that when executed cause one or more processors to:

store a first set of one or more parameters for a first set of one or more therapeutic electrical stimulation signals;

determine one or more local field potential (LFP) measurements of an LFP, wherein the LFP is of a first signal type that is intrinsically generated by a signal source within a brain of a patient;

cause delivery of one or more electrical stimulation signals;

determine one or more evoked resonant neural activity (ERNA) signals that are evoked by delivery of respective ones of the one or more electrical stimulation signals, wherein the ERNA signals are of a second type that is different than the first signal type of the LFP;

determine a second set of one or more parameters for a second set of one or more therapeutic electrical stimulation signals based on the one or more evoked signals having the second signal type and the one or more LFP measurements of the LFP having the first signal type, wherein the second set of one or more parameters are updates to the first set of one or more parameters; and cause delivery of the second set of the one or more therapeutic electrical stimulation signals.

26. The method of claim 14, wherein a respective evoked signal of the one or more evoked signals is not present within the brain prior to delivery of a respective electrical stimulation signal that evoked the respective evoked signal.

* * * * *